（12) United States Patent
Mizuno et al.

(10) Patent No.: US 7,057,036 B2
(45) Date of Patent: Jun. 6, 2006

(54) PYRROLOTHIAZINE AND PYRROLOTHIAZEPINE COMPOUNDS HAVING SEROTONIN-2 RECEPTOR ANTAGONISTIC AND ALPHA-1-BLOCKING ACTION

(75) Inventors: Akira Mizuno, Kyoto (JP); Makoto Shibata, Ashikaga (JP); Tomoe Kamei, Takatsuki (JP); Harukazu Fukami, Kyoto (JP); Norio Inomata, Mino (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 115 days.

(21) Appl. No.: 10/615,836

(22) Filed: Jul. 10, 2003

(65) Prior Publication Data

Related U.S. Application Data

(62) Division of application No. 09/871,655, filed on Jun. 4, 2001, now Pat. No. 6,624,314, which is a division of application No. 09/367,841, filed as application No. PCT/JP98/05954 on Dec. 25, 1998, now Pat. No. 6,271,223.

(30) Foreign Application Priority Data

Dec. 26, 1997 (JP) .................................. 9-366756

(51) Int. Cl.
*C07D 267/02* (2006.01)
*C07D 513/00* (2006.01)
*C07D 207/00* (2006.01)
(52) U.S. Cl. ......................... 540/552; 544/48; 548/541
(58) Field of Classification Search ................. 540/552; 544/48; 548/541
See application file for complete search history.

(56) References Cited

U.S. PATENT DOCUMENTS

| 5,075,440 A | 12/1991 | Wustrow et al. |
| 5,206,239 A | 4/1993 | Mizuno et al. |
| 5,391,731 A | 2/1995 | Mizuno et al. |
| 5,397,780 A | 3/1995 | Mizuno et al. |

(Continued)

FOREIGN PATENT DOCUMENTS

HU      218 909      12/2000

(Continued)

OTHER PUBLICATIONS

Mizuno, Tetrahedron Letters 41(34) 6605-9 2000.

*Primary Examiner*—Deborah C. Lambkin
(74) *Attorney, Agent, or Firm*—Oblon, Spivak, McClelland, Maier & Neustadt, P.C.

(57) ABSTRACT

A pyrrolesulfonamide derivative having the following formula (I):

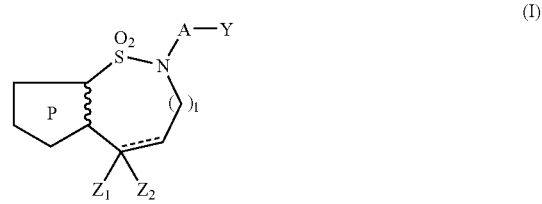

wherein the ring P represented by

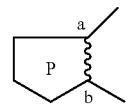

is a pyrrole ring having the following structure:

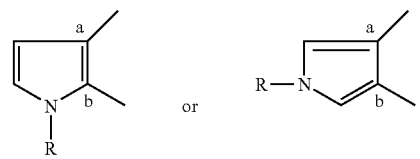

wherein R represents alkyl, cycloalkyl, cycloalkyl-alkyl or aralkyl; the dashed line indicates the presence or absence of a bond; and, when the bond is present, $Z_2$ is not present and $Z_1$ represents H but, when the bond is absent, $Z_1$ represents H and $Z_2$ represents OH or $Z_1$ and $Z_2$ are combined together to represent O or a group $NOR_1$, in which $R_1$ represents H, or alkyl, aralkyl or aryl; l stands for 0 or 1; A represents alkylene, alkenylene or alkynylene; and Y represents a group

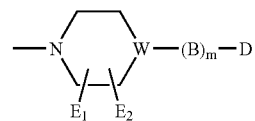

in which W represents CH, C= or N; m stands for 0 or 1 when W is CH or N, or m stands for 1 when W is C=; B represents a specific divalent group; $E_1$ and $E_2$ each independently represents H or lower alkyl; and D represents an aromatic hydrocarbon group or heterocyclic group. The compound (I) has strong serotonin-2 receptor antagonistic action and low toxicity and less side effects, and is useful as a therapeutic for circulatory diseases such as ischemic heart diseases, cerebrovascular disturbances and peripheral circulatory disturbances.

12 Claims, No Drawings

U.S. PATENT DOCUMENTS

| | | |
|---|---|---|
| 5,399,557 A | 3/1995 | Mizuno et al. |
| 5,416,082 A | 5/1995 | Mizuno et al. |
| 5,684,161 A | 11/1997 | Imoto et al. |
| 5,817,652 A * | 10/1998 | Brieaddy et al. ...... 514/211.09 |
| 5,962,448 A | 10/1999 | Mizuno et al. |
| 6,187,772 B1 | 2/2001 | Mizuno et al. |
| 6,211,362 B1 | 4/2001 | Mizuno et al. |
| 6,258,805 B1 | 7/2001 | Mizuno et al. |
| 6,271,223 B1 | 8/2001 | Mizuno et al. |
| 6,331,623 B1 * | 12/2001 | Mizuno et al. ............. 540/484 |
| 236,765 A1 | 4/2003 | Mizuno et al. |
| 6,583,296 B1 * | 6/2003 | Mizuno et al. ............. 548/541 |
| 240,178 A1 | 7/2003 | Mizuno et al. |
| 208,631 A1 | 9/2003 | Mizuno et al. |
| 6,624,314 B1 | 9/2003 | Mizuno et al. |
| 6,743,913 B1 * | 6/2004 | Mizuno et al. ............. 540/552 |

FOREIGN PATENT DOCUMENTS

| WO | WO 99/33840 | 7/1999 |
|---|---|---|

* cited by examiner

US 7,057,036 B2

PYRROLOTHIAZINE AND PYRROLOTHIAZEPINE COMPOUNDS HAVING SEROTONIN-2 RECEPTOR ANTAGONISTIC AND ALPHA-1-BLOCKING ACTION

TECHNICAL FIELD

This invention relates to novel pyrrolesulfonamide derivatives. More specifically, this invention is concerned with pyrrolo[2,3-e][1,2]thiazine derivatives, pyrrolo[3,4-e][1,2]thiazine derivatives, pyrrolo[2,3-f][1,2]thiazepine derivatives and pyrrolo[3,4-f][1,2]thiazepine derivatives, and salts thereof, said derivatives and salts having strong serotonin-2 receptor antagonistic action of excellent selectivity and being useful, for example, for the prevention or treatment of ischemic heart diseases such as angina pectoris, arrhythmia, myocardial infarction, congestive heart failure and post-PTCA restenosis, cerebrovascular disturbances such as cerebral infarction and cerebral sequelae after subarachnoid hemorrhage, peripheral circulatory disturbances such as arteriosclerosis obliterans, thromboangiitis obliterans and Raynaud disease, and hypertension; their preparation processes; and pharmaceuticals containing them as effective ingredients.

BACKGROUND ART

Serotonin is a compound contained abundantly in platelets, which are a blood component, and in a central nervous system, it acts as a neurotransmitter. In platelets, it is released upon stimulation by thromboxane $A_2$, ADP, collagen or the like, and synergistically acts on release of various platelet aggregation factors through activation of serotonin-2 receptors in the platelets and vascular smooth muscle cells and also on vasoconstriction by norepinephrine through $\alpha_1$ receptors, thereby inducing strong platelet aggregation and vasoconstriction [P. M. Vanhoutte, "Journal of Cardiovascular Pharmacology", Vol. 17 (Supple. 5), S6–S12 (1991)].

Serotonin is also known to potentiate proliferation of vascular smooth muscle cells [S. Araki et al., "Atherosclerosis", Vol. 83, pp. 29–34 (1990)]. It has been considered that, particularly when endothelial cells are injured as in arteriosclerosis or myocardial infarction, the vasoconstricting action and thrombus forming action of serotonin are exasperated, thereby reducing or even stopping blood supply to myocardial, cerebral and peripheral organs [P. Golino et al., "The New England Journal of Medicine", Vol. 324, No. 10, pp. 641–648 (1991), Y. Takiguchi et al., "Thrombosis and Haemostasis", Vol. 68(4), pp. 460–463 (1992), A. S. Weyrich et al., "American Journal of Physiology", Vol. 263, H349–H358 (1992)]. Being attracted by such actions of serotonin or serotonin-2 receptors, various attempts are now under way to use a serotonin-2 receptor antagonist as a pharmaceutical for ischemic diseases of the heart, the brain and peripheral tissues.

Several compounds, led by sarpogrelate, are known to have serotonin-2 receptor antagonistic action. They however do not include anything having the pyrrolo[2,3-e][1,2]thiazine skeleton, pyrrolo[3,4-e][1,2]thiazine skeleton, pyrrolo[2,3-f][1,2]thiazepine skeleton or pyrrolo[3,4-f][1,2]thiazepine skeleton. Those known to have serotonin-2 receptor antagonistic action are accompanied with many problems to be improved in potency, toxicity, side effects or the like. On the other hand, medicines which have anti-serotonin action and $\alpha_1$-blocking action in combination are considered to become extremely effective medicines for the treatment and prevention of hypertension and ischemic heart diseases, because they have possibility to reduce side effects, such as orthostatic hypotension and reflex tachycardia, induced by antihypertensive action on the basis of the $\alpha_1$-blocking action and hypertension is a serious risk factor for ischemic heart diseases.

DISCLOSURE OF THE INVENTION

In view of the foregoing circumstances, the present inventors have proceeded with extensive research toward compounds which have strong serotonin-2 receptor antagonistic action and low toxicity and less side effects and are useful for the treatment and prevention of ischemic heart diseases, cerebrovascular disturbances and peripheral circulatory disturbances. As a result, it has been found that pyrrolesulfonamides represented by the below-described formula (I) meet the above conditions. It has also been found that the compounds according to the present invention include those also having $\alpha_1$-blocking action in combination and that such compounds are useful as antihypertensives or the like having less side effects and are widely usable for the treatment and prevention of circulatory diseases.

The present invention has been completed based on the above described findings. A first object of the present invention is to provide a pyrrolesulfonamide derivative or a salt thereof, said pyrrolesulfonamide derivative being represented by the following formula (I):

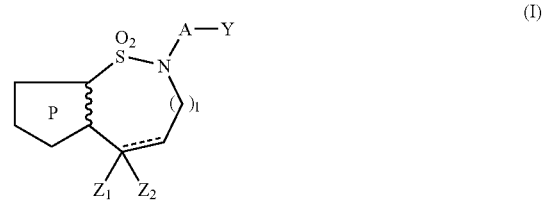

wherein
the ring P represented by

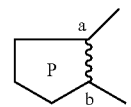

means a pyrrole ring represented by the following structure:

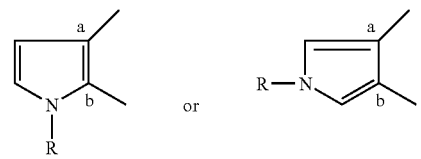

in which R represents an alkyl group, a cycloalkyl group, a cycloalkyl-alkyl group or a substituted or unsubstituted aralkyl group;

the dashed line indicates the presence or absence of a bond; and, when the bond indicated by the dashed line is present, $Z_2$ is not present and $Z_1$ represents a hydrogen atom but, when the bond indicated by the dashed line is absent, $Z_1$ represents a hydrogen atom and $Z_2$ represents a hydroxyl group; or $Z_1$ and $Z_2$ are combined together to represent an oxygen atom or a group $NOR_1$ in which $R_1$ represents a hydrogen atom, a substituted or unsubstituted alkyl group, a substituted or unsubstituted aralkyl group or a substituted or unsubstituted aryl group;

l represents 0 or 1;

A represents a substituted or unsubstituted alkylene group, a substituted or unsubstituted alkenylene group or a substituted or unsubstituted alkynylene group; and Y represents a group

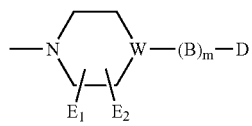

in which W represents CH, C= or a nitrogen atom; and, when W represents CH, m stands for 0 or 1, B represents a carbonyl group, a sulfonyl group, an alkylene group, an alkenylene group, a group —C(OH)$R_2$— in which $R_2$ represents a substituted or unsubstituted aryl group, a group —$CHR_3$— in which $R_3$ represents a substituted or unsubstituted aryl group, or a substituted or unsubstituted cyclic or acyclic acetal group; when W represents C=, m stands for 1, B represents a group

in which the double bond is coupled with W and $R_4$ represents a substituted or unsubstituted aryl group or a substituted or unsubstituted aralkyl group; when W represents a nitrogen atom, m stands for 0 or 1, and B represents a carbonyl group, a sulfonyl group, an alkylene group, an alkenylene group or a group —$CHR_5$— in which $R_5$ represents a substituted or unsubstituted aryl group; $E_1$ and $E_2$ each independently represents a hydrogen atom or a lower alkyl group; and D represents a substituted or unsubstituted aromatic hydrocarbon group or a substituted or unsubstituted aromatic heterocyclic group.

Another object of the present invention is to provide a preparation process of the pyrrolesulfonamide derivative (I) or its salt.

A further object of the present invention is to provide a pharmaceutical which comprises the pyrrolesulfonamide derivative (I) or its pharmaceutically-acceptable salt as an effective ingredient and is usable for the treatment or the like of circulatory diseases.

BEST MODES FOR CARRYING OUT THE INVENTION

In the pyrrolesulfonamide derivatives (I) of the present invention, the ring P represents one of the following pyrrole rings:

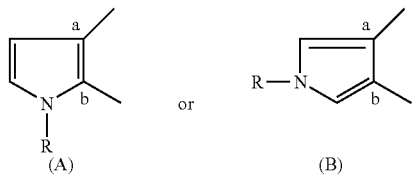

wherein R has the same meaning as defined above.

Preferred examples of the group R bonded to the nitrogen atom of the pyrrole ring can include linear or branched alkyl groups having 1–8 carbon atoms preferably, such as methyl, ethyl, n-propyl, isopropyl and n-pentyl; cycloalkyl groups having 3–8 carbon atoms, such as cyclopropyl, cyclopentyl and cyclohexyl; cycloalkyl-alkyl groups having 4–8 carbon atoms, such as cyclopropylmethyl, cyclohexylmethyl and cyclohexylethyl; and aralkyl groups having 7–22 carbon atoms, such as diphenylmethyl, benzyl and phenethyl. For example, one or more hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy. Among these, particularly preferred are methyl and ethyl.

Further, l stands for 0 or 1 in the compound (I) according to the present invention. As the combination between the ring P and l, preferred examples can be (A) and 1, (A) and 0, and (B) and 1. Of these, the combinations of (A) and 1 and (A) and 0 are particularly preferred.

On the other hand, preferred examples of the group A in the compound (I) according to the present invention can include linear or branched alkylene groups having 2–10 carbon atoms, such as ethylene, trimethylene, tetramethylene, pentamethylene and octamethylene; linear or branched alkenylene groups having 4–10 carbon atoms, such as 2-butenylene and 3-pentenylene; and linear or branched alkynylene groups having 4–10 carbon atoms, such as 2-butynylene and 3-pentynylene. One or more of the hydrogen atoms of each of these groups may be substituted by a like number of halogen atoms such as fluorine, chlorine and/or bromine atoms. Among the above groups, trimethylene and tetramethylene are particularly preferred.

Further, preferred examples of the group $Z_1$ and the group $Z_2$ in the compound (I) according to the present invention can include the following combinations: when the bond indicated by the dashed line is present, $Z_2$ is not present and $Z_1$ represents a hydrogen atom; when the bond indicated by the dashed line is absent, $Z_1$ represents a hydrogen atom and $Z_2$ represents a hydroxyl group, or $Z_1$ and $Z_2$ are combined together to represent an oxygen atom or the group $NOR_1$.

Preferred examples of $R_1$ in the group $NOR_1$ can include a hydrogen atom; linear or branched alkyl groups having 1–4 carbon atoms preferably, such as methyl and ethyl; aryl groups having 6–14 carbon atoms, such as phenyl and naphthyl; and aralkyl groups having 7–22 carbon atoms, such as benzyl and phenethyl. One or more of the hydrogen atoms of each of these groups may be substituted by a like number of halogen atoms such as fluorine, chlorine and/or bromine atoms, alkyl groups having 1–4 carbon atoms preferably, such as methyl and/or ethyl, and/or alkoxy groups having 1–4 carbon atoms preferably, such as methoxy and/or ethoxy. Of these, hydrogen atom and methyl group are particularly preferred.

In the compound (I) according to the present invention, Y is a group

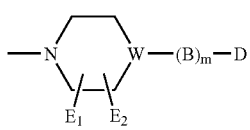

wherein B, D, $E_1$, $E_2$, W and m have the same meanings as defined above. The group represented by the following formula:

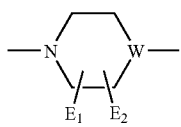

wherein $E_1$, $E_2$ and W have the same meanings as defined above is a heterocyclic group derived from piperidine or piperazine, and two or less of the hydrogen atoms on the ring may be substituted by a like number of alkyl groups having 1–4-carbon-atoms preferably, such as methyl and/or ethyl.

When the above group is a heterocyclic group derived from piperidine, m stands for 0 or 1 (with the proviso that m stands for 1 when W represents C=), and B represents a carbonyl group, a sulfonyl group, an alkylene group (an alkylene group having 1–4 carbon atoms preferably, with a methylene group being particularly preferred), an alkenylene group (an alkenylene group having 2–5 carbon atoms preferably, with a 2-propenylene group being particularly preferred), a group —C(OH)$R_2$— in which $R_2$ is an aryl group having 6–14 carbon atoms, such as phenyl or naphthyl, in which one or more of the hydrogen atoms may be substituted, a group —CHR$_3$— in which $R_3$ is an aryl group having 6–14 carbon atoms, such as phenyl or naphthyl, in which one or more of the hydrogen atoms may be substituted, a group

in which the double bond is coupled with W, $R_4$ represents an aryl group having 6–14 carbon atoms, such as phenyl or naphthyl, or an aralkyl group having 7–22 carbon atoms, such as benzyl or phenethyl, and these groups may be in substituted forms, or a cyclic or acyclic acetal-group in which one or more of the hydrogen atoms may be substituted.

Exemplary cyclic or acyclic acetal groups include:

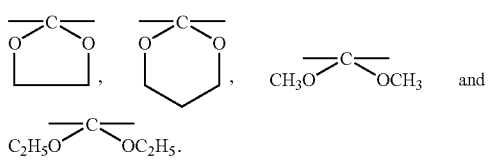

In the above-described definition of B, preferred examples of substituents on the groups $R_2$, $R_3$ and $R_4$ can include one or more alkyl groups having 1–4 carbon atoms, such as methyl and ethyl; aryl groups having 6–14 carbon atoms, such as phenyl and naphthyl; halogen atoms such as fluorine atoms, chlorine atoms and bromine atoms; alkoxy groups having 1–4 carbon atoms, such as methoxy and ethoxy; hydroxyl groups; cyano groups; and nitro groups.

Further, illustrative of substituents on the cyclic or acyclic acetal are halogen atoms such as fluorine atoms, chlorine atoms, and bromine atoms; alkyl groups having 1–4 carbon atoms, such as methyl and ethyl; aryl groups having 6–14 carbon atoms, such as phenyl and naphthyl; aralkyl groups having 7–22 carbon atoms, such as benzyl and phenethyl; and alkylidene groups having 1–4 carbon atoms preferably, such as methylidene and ethylidene.

As a particularly preferred example of B, a carbonyl group can be mentioned.

When the heterocyclic group is a group derived from piperazine, m stands for 0 or 1 (preferably 0), and B represents a carbonyl group, a sulfonyl group, an alkylene group (preferably, an alkylene group having 1–4 carbon atoms, with a methylene group being particularly preferred), an alkenylene group (preferably, an alkenylene group having 3–6 carbon atoms, with a 2-propenylene group being particularly preferred), a group —CHR$_5$— in which $R_5$ represents an aryl group having 6–14 carbon atoms, such as phenyl or naphthyl.

The above-described $R_5$ may be substituted further, for example, by one or more of halogen atoms such as fluorine, chlorine and/or bromine, alkyl groups having 1–4 carbon atoms preferably, such as methyl and/or ethyl, alkoxy groups having 1–4 carbon atoms preferably, such as methoxy and/or ethoxy, hydroxyl groups, and/or the like.

As a preferred example of the above-described B, a substituted or unsubstituted phenylmethylene group can be mentioned.

Preferred examples of group D can include aromatic hydrocarbon groups having 6–28 carbon atoms preferably, such as a phenyl group in which one or more of the hydrogen atoms may be substituted and a naphthyl group in which one or more of the hydrogen atoms may be substituted.

Other preferred examples of D can include aromatic heterocyclic groups, preferably those each of which is monocyclic or bicyclic and contains three or less hetero atoms, such as pyridyl, pyrimidinyl, benzisothiazolyl, benzisoxazolyl, indazolyl and indolyl groups in which one or more of hydrogen atoms may be substituted. Examples of the hetero atoms can include oxygen, sulfur and nitrogen atoms.

Examples of the substituents for the above aromatic hydrocarbon group or aromatic heterocyclic group can include halogen atoms such as fluorine, chlorine and bromine; alkyl groups having 1–4 carbon atoms preferably, such as methyl and ethyl; alkoxyl groups having 1–4 carbon atoms preferably, such as methoxy and ethoxy; aryl groups having 6–14 carbon atoms, such as phenyl and naphthyl; aralkyl groups having 7–22 carbon atoms, such as benzyl and phenethyl; aralkyloxy groups having 7–22 carbon atoms preferably, such as benzyloxy; cyano groups; nitro groups; carboxyl groups; alkoxycarbonyl groups (with an alcohol moiety thereof having 1–6 carbon atoms preferably); lower alkylsulfonylamino groups (with an alkyl moiety thereof having 1–4 carbon atoms preferably); carbamoyl groups; and hydroxyl groups.

Among these examples of group D, preferred ones can include phenyl groups which may be unsubstituted or substituted by one or more of halogen atoms, alkoxy groups and/or hydroxyl groups; benzisothiazolyl groups which may be unsubstituted or substituted by one or more halogen atoms; benzisoxazolyl groups which may be unsubstituted or substituted by one or more halogen atoms; and indazolyl groups which may be unsubstituted or substituted by one or more halogen atoms. Particularly preferred are an unsubstituted phenyl group; and phenyl groups substituted by one or more of fluorine atoms, methoxy groups and/or hydroxyl groups.

Many of the compounds (I) according to the present invention have isomers. It is to be noted that these isomers and mixtures thereof are all embraced by the present invention.

The pyrrolesulfonamide derivatives (I) according to the present invention can be prepared by various processes. It is however preferred to prepare each of them, for example, by using a pyrrolesulfonamide derivative (IIa) or (IIa'), which is available by Process 1 to be described below, and following any one of the processes to be described as Process 2 onwards.

Process 1:

Pyrrolesulfonamide derivatives (IIa) and (IIa') useful as starting materials can be synthesized, for example, by the following process:

Process (a)

Compounds represented by the formula (IIa) and (IIa') can be obtained in accordance with the following reaction scheme, namely, by converting a 1-substituted pyrrole-3-sulfonic acid represented by the formula (XII) or a salt thereof into a 1-substituted pyrrole-3-sulfonyl halide represented by the formula (XIII), reacting glycine, β-alanine or a derivative thereof represented by the formula (XIV) or an organic or inorganic acid salt thereof with the compound (XIII) and, if necessary, conducting deprotection to obtain a compound represented by the formula (XV) and then subjecting the thus-obtained compound to a ring-closing reaction.

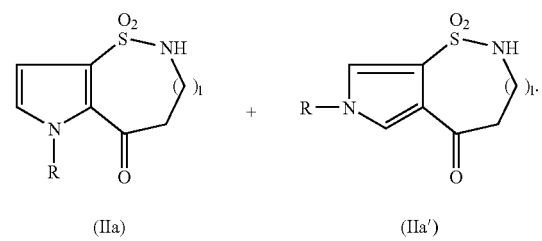

(IIa)　　　　　　　　　　(IIa')

wherein M represents a hydrogen ion, an alkali metal ion, an alkaline earth metal ion or a quaternary ammonium ion, p stands for 1 when M represents a hydrogen ion, an alkali metal ion or a quaternary ammonium ion or p stands for 2 when M represents an alkaline earth metal ion, q stands for 0 or 1, $R_6$ represents a hydrogen atom or a carboxyl-protecting group, X" represents a chlorine atom or a bromine atom, and R and l have the same meanings as defined above.

Illustrative of M in the compound represented by the formula (XII) in the above scheme are hydrogen ion; alkali metal ions such as sodium ion and potassium ion; alkaline earth metal ions such as barium ion; and quaternary ammonium ions such as pyridinium ion. As representative preparation processes of the compound represented by the formula (XII), the following two processes can be mentioned.

[Preparation Process of the Compound (XII)-1]

The compound represented by the formula (XII) can be obtained in accordance with the following formula, namely, by causing a sulfonating agent such as sulfur trioxide-pyridine complex to act on a 1-substituted pyrrole (XVIII) and, if necessary, treating the resultant compound with an acid such as hydrochloric acid or sulfuric acid or a base such as sodium hydroxide, sodium carbonate, sodium hydrogencarbonate or barium hydroxide.

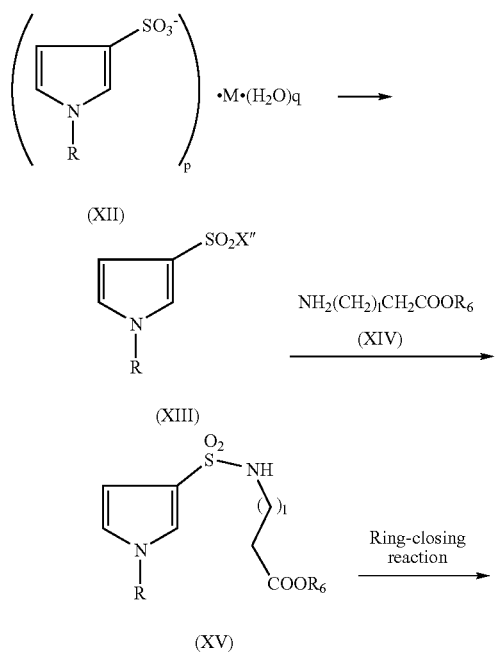

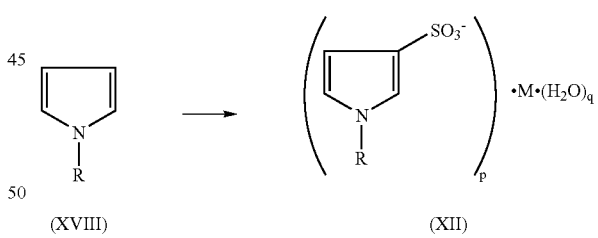

(XVIII)　　　　　　　　　(XII)

wherein M, R, p and q have the same meanings as defined above.

[Preparation Process of the Compound (XII)-2]

The compound represented by the formula (XII) can be obtained in accordance with the following formula, namely, by causing trimethylsilyl chlorosulfonate (XIX) to act on a 1-substituted-2-tri-n-butylstannylpyrrole represented by the formula (XVII) in a solvent, which does not take part in the reaction, such as carbon tetrachloride or 1,2-dichloroethane and then hydrolyzing the resultant compound. Here, a basic substance may be allowed to exist concurrently, whereby the reaction product can be obtained as a salt.

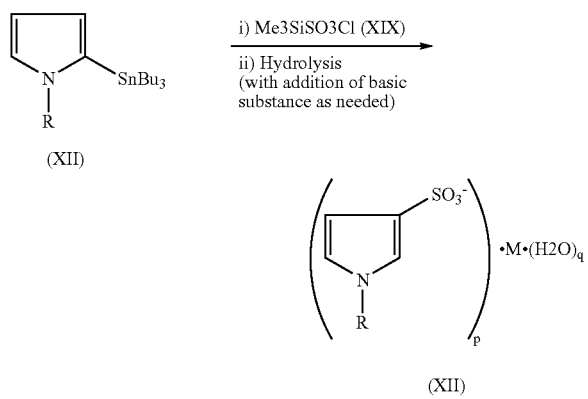

(XII)

wherein M, R, p and q have the same meanings as defined above.

Further, the compound (XIII) can be obtained by causing phosphorus pentachloride or phosphorus pentabromide to act on the compound (XII) in a solvent which does not take part in the reaction, such as ethyl ether or toluene.

In addition, as the carboxyl-protecting group represented by the group $R_6$ in the compound (XIV), it is possible to use, in addition to lower alkyl groups such as methyl, ethyl, n-propyl, isopropyl, n-butyl, isobutyl and t-butyl and aralkyl groups having 7–20 carbon atoms, such as benzyl and 9-anthrylmethyl, conventional protecting groups such as those described in T. W. Greene: "Protective Groups in organic Synthesis" (John Wiley & Sons, Inc.) and the like.

Further, as an illustrative synthesis process of the compound (XV), a process can be mentioned in which a base is added to the compound (XIII), as needed, and glycine, β-alanine or a derivative thereof or an organic or inorganic acid salt thereof is caused to act. Usable examples of the base can include organic bases such as triethylamine and pyridine, and inorganic bases such as sodium hydrogencarbonate, potassium carbonate and sodium hydroxide.

The compound (XV) so obtained is subjected to a cyclizing reaction, optionally after removing the protecting group by virtue of a suitable method such as the action of an acid or a base, or catalytic reduction. This cyclizing reaction is conducted by treating the compound (XV) together with an organic acid such as methanesulfonic acid, an inorganic acid such as sulfuric acid or polyphosphoric acid or a mixture of such an organic or inorganic acid and phosphorus pentoxide at room temperature to 170° C., preferably at 80–120° C.

In this case, a solvent which does not take part in the reaction may be added as needed.

Further, the cyclizing reaction can also be practiced by, optionally after addition of a catalyst such as dimethylformamide to the compound (XV) in which $R_6$ is a hydrogen atom, treating the compound with oxalyl chloride, thionyl chloride, thionyl bromide, oxalyl bromide, phosgene, phosphorus trichloride, phosphorus tribromide, phosphoryl chloride, phosphoryl bromide or the like to convert it into its corresponding acid halide and then treating the acid halide at −20° C. to reflux temperature in the presence of a Lewis acid such as aluminum chloride, aluminum bromide, boron trifluoride-ether complex or tin tetrachloride in a solvent such as dichloromethane, 1,2-dichloroethane or nitromethane. In the above-described reactions, the compound (IIa) and the compound (IIa') can be formed at varied ratios by changing the reaction conditions.

Process (b)

Compounds represented by the formula (IIb) and (IIb') can be obtained in accordance with the following reaction scheme, namely, by converting a pyrrole-3-sulfonic acid represented by the formula (XX) or a salt thereof into a pyrrole-3-sulfonyl halide represented by the formula (XXI), reacting glycine, β-alanine or a derivative thereof represented by the formula (XIV) or an organic or inorganic acid salt thereof with the compound (XXI) and, if necessary, conducting deprotection to obtain a compound represented by the formula (XXII) and then subjecting the thus-obtained compound to a ring-closing reaction. The compound (IIa) and compound (IIa') can then be obtained by introducing groups R to the pyrrole-nitrogen atoms of the compounds (IIb), (IIb'), respectively.

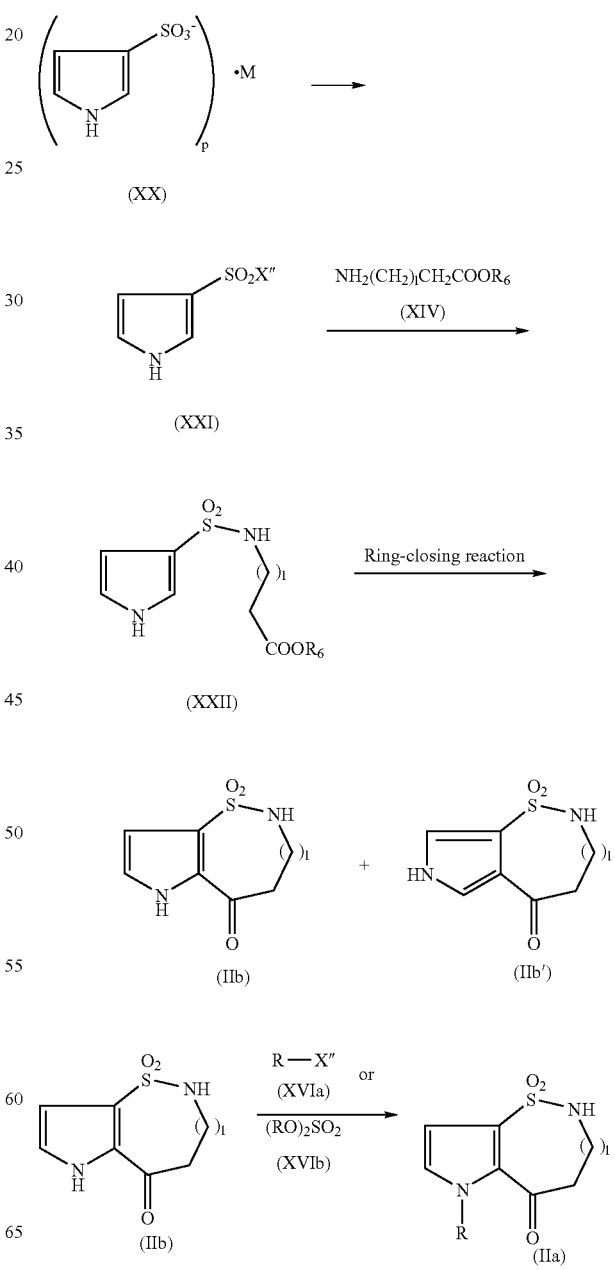

-continued

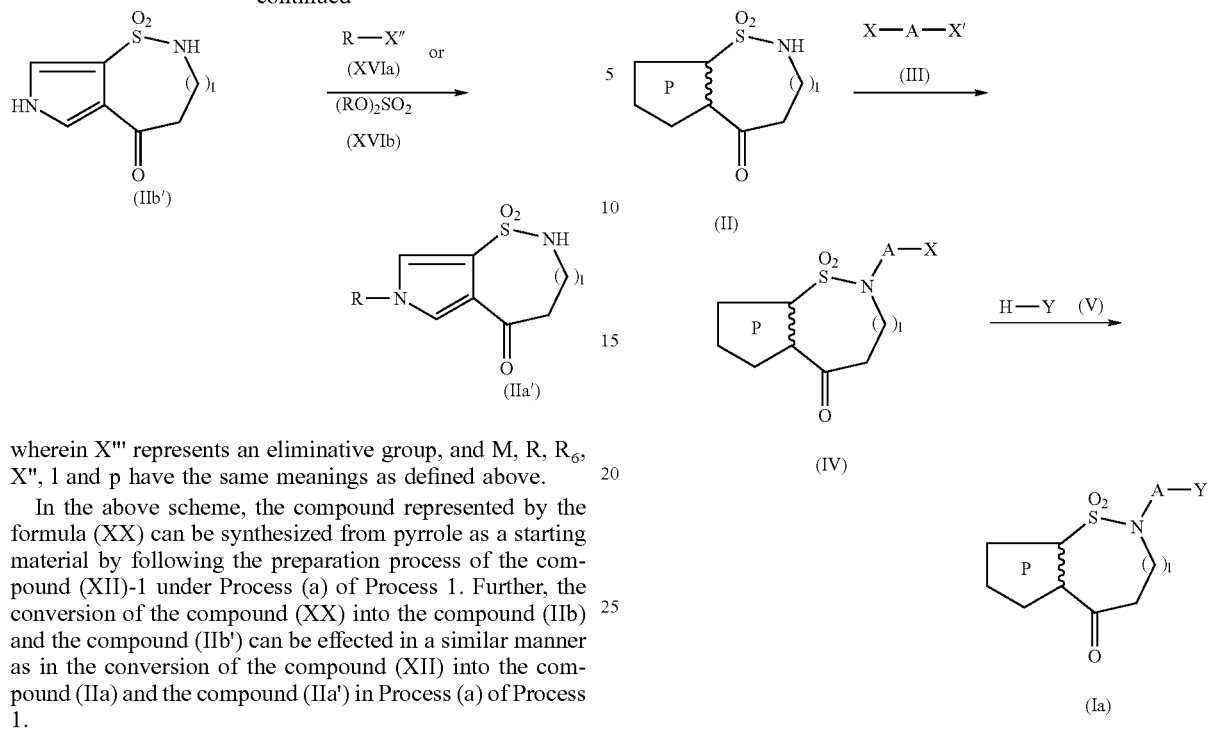

wherein X''' represents an eliminative group, and M, R, $R_6$, X'', l and p have the same meanings as defined above.

In the above scheme, the compound represented by the formula (XX) can be synthesized from pyrrole as a starting material by following the preparation process of the compound (XII)-1 under Process (a) of Process 1. Further, the conversion of the compound (XX) into the compound (IIb) and the compound (IIb') can be effected in a similar manner as in the conversion of the compound (XII) into the compound (IIa) and the compound (IIa') in Process (a) of Process 1.

The conversion from the compound (IIb) into the compound (IIa) can be effected by treating the compound (IIb) with an organic or inorganic base and then reacting the compound represented by the formula (XVIa) or (XVIb), or by causing the compound (XVIa) or the compound (XVIb) to act on the compound (IIb) in the presence of such a base.

Examples of the eliminative group represented by the group X''' in the compound (XVIa) can include halogen atoms such as chlorine, bromine and iodine, alkylsulfonyloxy groups such as methanesulfonyloxy, and arylsulfonyloxy groups such as p-toluenesulfonyloxy. Exemplary organic or inorganic bases can include potassium carbonate, sodium carbonate, potassium hydroxide, sodium hydroxide, sodium hydride, triethylamine, sodium methoxide, and potassium t-butoxide. Further, illustrative solvents usable in the above reaction include acetone, 2-butanone, acetonitrile, tetrahydrofuran, dioxane, dimethylformamide, and dimethylsulfoxide. The reaction is conducted at –20° C. to reflux temperature.

On the other hand, the conversion from the compound (IIb') into the compound (IIa') can also be effected under the same conditions as in the above-described conversion from the compound (IIb) into the compound (IIa).

Process 2:

Among the pyrrolesulfonamide derivatives (I), compounds (Ia) in each of which $Z_1$ and $Z_2$ are combined together to represent an oxygen atom can be synthesized, for example, by any one of the following processes.

Process (a)

Each compound (Ia) can be obtained in accordance with the following reaction scheme, namely, by reacting a compound represented by the formula (II) with a compound represented by the formula (III) to convert the compound (II) into a compound represented by the formula (IV) and then reacting a nitrogen-containing compound represented by the formula (V) or a salt thereof with the compound (IV).

wherein X and X' represent the same or different eliminative groups, and A, the ring P, Y and l have the same meanings as defined above.

In the above-described reaction, the conversion from the compound (II) into the compound (IV) can be effected by treating the compound (II) with an organic or inorganic base and then reacting the compound (III) with the compound (II), or by causing the compound (III) to act on the compound (II) in the presence of such a base.

The groups X and X' in the compound (III) are eliminative groups. Illustrative can be halogen atoms such as chlorine and bromine, alkylsulfonyloxy groups such as methanesulfonyloxy, and arylsulfonyloxy groups such as p-toluenesulfonyloxy.

Exemplary inorganic bases or organic bases can include sodium carbonate, potassium carbonate, sodium hydroxide, potassium hydroxide, sodium hydride, triethylamine, sodium ethoxide, sodium bis(trimethylsilyl)amide, and potassium t-butoxide. The reaction can be conducted at –78° C. to reflux temperature in a solvent which does not take part in the reaction.

To prepare the compound (Ia) from the thus-obtained compound (IV) and the nitrogen-containing compound (V), it is only necessary to react the nitrogen-containing compound (V) or an organic acid salt or inorganic acid salt thereof with the compound (IV), optionally together with an organic base such as triethylamine, pyridine, collidine or potassium t-butoxide or an inorganic base such as potassium carbonate, sodium carbonate, sodium hydrogencarbonate, sodium hydroxide or sodium hydride and optionally with the addition of an alkali iodide such as potassium iodide or sodium iodide, in a solventless manner or in a solvent such as acetone, 2-butanone, acetonitrile, dimethylformamide, methanol, ethanol or the like at room temperature to 150° C.

Examples of the nitrogen-containing compound (V) can include 1-phenylpiperazine, 1-(2-fluorophenyl)piperazine, 1-(3-fluorophenyl)piperazine, 1-(4-fluorophenyl)piperazine, 1-(4-hydroxyphenyl)piperazine, 1-(2-chlorophenyl)piperazine, 1-(3-chlorophenyl)piperazine, 1-(4-chlorophenyl)piperazine, 1-(2-methoxyphenyl)piperazine, 1-(3-methoxyphenyl)piperazine, 1-(4-methoxyphenyl)piperazine, 1-(4-methanesulfonamidophenyl)piperazine, 1-(4-cyanophenyl)piperazine, 1-(4-carbamoylphenyl)piperazine, 1-(4-methoxycarbonylphenyl)piperazine, 1-(2-pyridyl)piperazine, 1-(2-pyrimidinyl)piperazine, 1-benzylpiperazine, 1-diphenylmethylpiperazine, 1-cinnamylpiperazine, 1-benzoylpiperazine, 1-(4-benzyloxybenzoyl)piperazine, 1-(4-hydroxybenzoyl)piperazine, 1-(2-furoyl)piperazine, 1-(1,2-benzisoxazol-3-yl)piperazine, 4-phenylpiperidine, 4-benzylpiperidine, α,α-bis(4-fluorophenyl)-4-piperidinemethanol, 4-(4-fluorobenzoyl)piperidine, 4-benzoylpiperidine, 4-(4-methoxybenzoyl)piperidine, 4-(4-chlorobenzoyl)piperidine, 4-(6-fluoro-1,2-benzisoxazol-3-yl)piperidine, 4-(6-fluoro-1H-indazol-3-yl)piperidine, 4-[(4-fluorophenyl)sulfonyl]piperidine, 4-[bis(4-fluorophenyl)methylene]piperidine, and 4-(4-fluorobenzoyl)piperidine ethylene acetal.

These compounds are either known in the art or readily available by processes known per se in the art or by processes similar to such known processes.

Process (b)

Further, the compound (Ia) can also be obtained by causing a nitrogen-containing compound represented by the formula (VI) to act on the compound represented by the formula (II) in accordance with the following reaction formula:

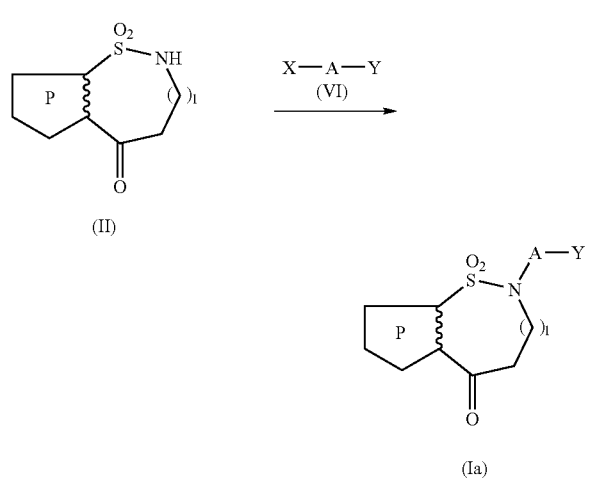

wherein A, the ring P, X, Y and l have the same meanings as defined above.

The conversion from the compound (II) into the compound (Ia) is conducted by causing the compound (VI) to act either after treatment of the compound (II) with an inorganic base or an organic base or in the presence of an inorganic base or an organic base. Reaction conditions are similar to those employed upon conversion from the compound (II) into the compound (IV) and described above under Process (a) of Process 2. Further, the compound (VI) can be synthesized by reacting the compound (III) with the compound (V) in a manner known per se in the art.

Process 3:

Among the pyrrolesulfonamide derivatives (I), the compounds (Ic) and (Ie) in each of which $Z_1$ and $Z_2$ are combined together to represent a group $NOR_1$ can each be synthesized by any one of the following processes.

Process (a)

Each compound (Ie) is obtained in accordance with the following reaction scheme, namely, by causing hydroxylamine or a derivative thereof (VII) or a salt thereof to act on a compound represented by the formula (IV) and then causing a nitrogen-containing compound (V) to act.

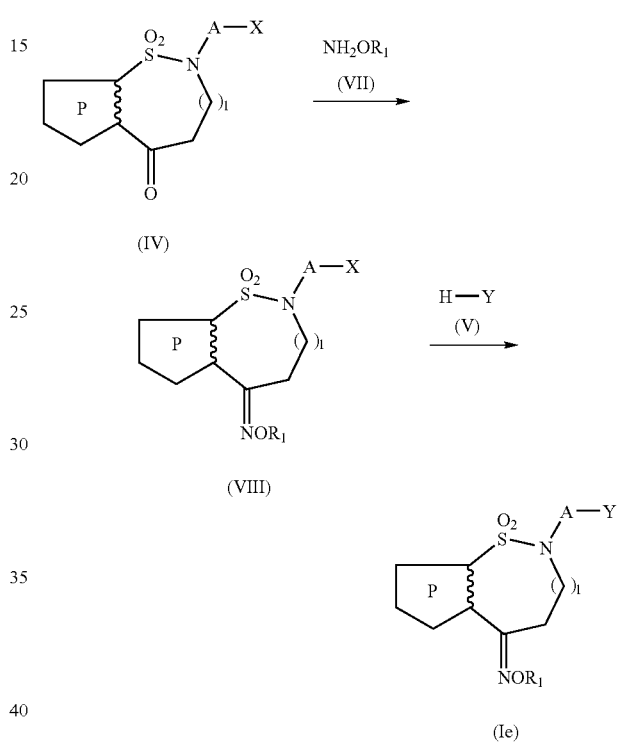

wherein A, the ring P, $R_1$, X, Y and l have the same meanings as defined above.

The reaction between the compound (IV) and the hydroxylamine or its derivative (VII) is effected, if necessary, in the presence of an organic base such as pyridine, triethylamine, collidine or sodium acetate or an inorganic base such as potassium carbonate or sodium hydroxide. The hydroxylamine or its derivative (VII) may also be used in the form of an organic acid salt or an inorganic acid salt.

The reaction is conducted at 0° C. to reflux temperature, preferably 0° C.–100° C. by using a suitable solvent, for example, methanol, ethanol, propanol, tetrahydrofuran, dimethylformamide or dimethylsulfoxide as needed.

Further, the conversion from the thus-obtained compound (VIII) into the compound (Ie) can be effected under similar conditions as in the conversion from the compound (IV) into the compound (Ia) shown above under Process (a) of Process 2.

Process (b)

Each compound (Ic) is obtained by causing hydroxylamine or its derivative (VII) or a salt thereof to act on a compound (Ib) in accordance with the following reaction formula.

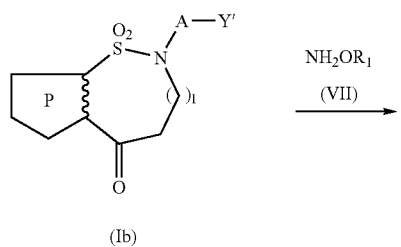

(Ib)

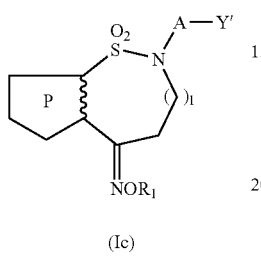

(Ic)

wherein A, the ring P, $R_1$ and l have the same meanings as defined above, and Y' represents a group

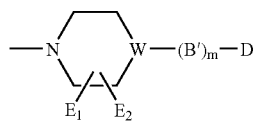

in which when W represents CH, B' represents a sulfonyl group, an alkylene group, an alkenylene group, a group —C(OH)$R_2$— in which $R_2$ represents a substituted or unsubstituted aryl group, a group —CHR$_3$— in which $R_3$ represents a substituted or unsubstituted aryl group, or a substituted or unsubstituted cyclic or acyclic acetal group; when W represents C=, B' represents a group

in which the double bond is coupled with W and $R_4$ represents a substituted or unsubstituted aryl group or a substituted or unsubstituted aralkyl group; when W represents a nitrogen atom, B' represents a carbonyl group, a sulfonyl group, an alkylene group, an alkenylene group or a group —CHR$_5$— in which $R_5$ represents a substituted or unsubstituted aryl group; and D, $E_1$, $E_2$ and m have the same meanings as defined above.

The conversion from the compound (Ib) into the compound (Ic) can be effected under similar conditions as the conversion from the compound (IV) into the compound (VIII) shown above under Process (a) of Process 3.

Process 4:

Among the pyrrolesulfonamide derivatives (I), the compounds (Id) and (If) in each of which $Z_1$ represents a hydrogen atom and $Z_2$ represents a hydroxyl group can each be synthesized by any one of the following processes.

Process (a)

Each compound (If) is obtained in accordance with the following reaction scheme, namely, by reducing a compound represented by the formula (IV) and then causing a nitrogen-containing compound (V) to act.

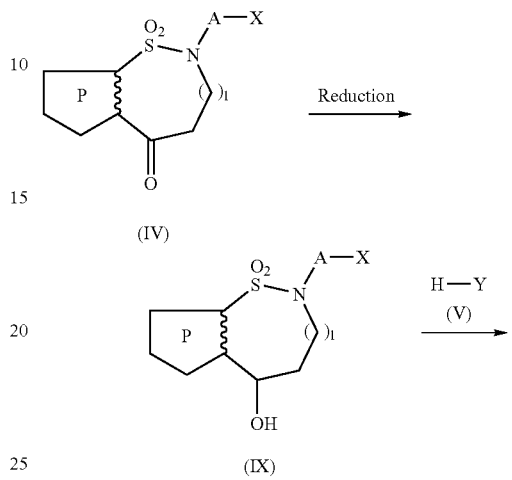

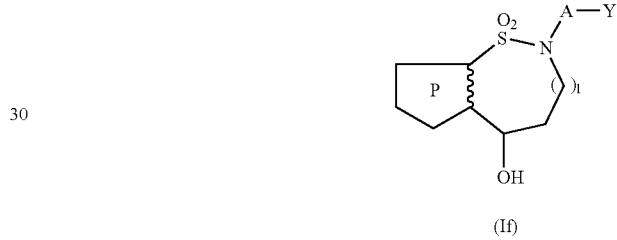

wherein A, the ring P, X, Y and l have the same meanings as defined above.

The conversion from the compound (IV) into the compound (IX) is conducted by treating the compound represented by the formula (IV) with a reducing agent such as sodium borohydride, potassium borohydride or sodium cyanoborohydride at −78° C. to reflux temperature, preferably −20° C. to room temperature in a conventionally used solvent.

The conversion from the compound (IX) into the compound (If) can be effected under similar conditions as the conversion from the compound (IV) into the compound (Ia) shown above under Process (a) of Process 2.

Process (b)

Each compound (Id) is obtained by reducing a compound represented by the formula (Ib) in accordance with the following reaction formula.

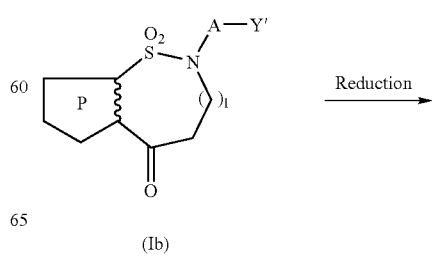

(Ib)

-continued

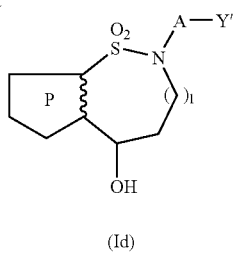

(Id)

wherein A, the ring P, Y' and l have the same meanings as defined above.

The conversion from the compound (Ib) into the compound (Id) can be effected under similar conditions as in the conversion from the compound (IV) into the compound (IX) shown above under Process (a) of Process 4.

Process 5:

Among the pyrrolesulfonamide derivatives (I), the compounds (Ig) in each of which the bond indicated by the dashed line is present and $Z_1$ represents a hydrogen atom can be synthesized by any one of the following processes.

Process (a)

Each compound (Ig) is obtained in accordance with the following reaction-scheme, namely, by subjecting a compound represented by the formula (IX) to a dehydration reaction to obtain a compound represented by the formula (X) and then causing a nitrogen-containing compound (V) to act on the compound (X).

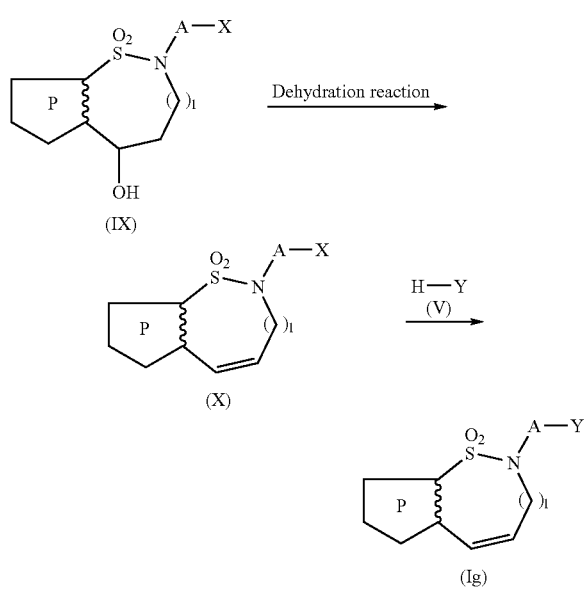

wherein A, the ring P, X, Y and l have the same meanings as defined above.

In the above-described reaction, the conversion from the compound (IX) into the compound (X) can be effected by treating the compound (IX) with an acid such as hydrogen chloride, hydrogen bromide, sulfuric acid, methanesulfonic acid or p-toluenesulfonic acid at −20° C. to 100° C., preferably at −20° C. to room temperature in a solvent such as water, methanol, ethanol, ethyl acetate, chloroform or toluene.

As an alternative, the conversion into the compound (X) can also be effected by causing methanesulfonyl chloride, p-toluenesulfonyl chloride, phosphorus trichloride, phosphorus oxychloride, thionyl chloride or the like and a base such as triethylamine, pyridine or collidine to act on the compound (IX), if necessary, in a solvent such as dichloromethane, chloroform or toluene.

The conversion from the compound (X) into the compound (Ig) can be effected under similar conditions as in the conversion from the compound (IV) into the compound (Ia) described above under Process (a) of Process 2.

Process (b)

Each compound (Ig) is obtained by subjecting a compound represented by the formula (If) to a dehydration reaction in accordance with the following reaction formula:

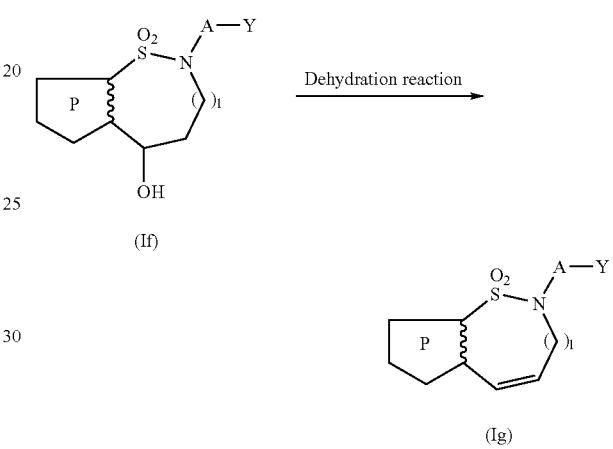

wherein A, the ring P, Y and l have the same meanings as defined above.

In the above-described reaction, the conversion from the compound (If) into the compound (Ig) can be effected under similar conditions as in the conversion from the compound (IX) into the compound (X) described above under Process (a) of Process 5.

If necessary, the compounds (I) of the present invention obtained according to the above-described processes can each be reacted with one of various acids to convert the compound into its salt. Then, the resulting salt can be purified by a method such as recrystallization or column chromatography.

Exemplary acids usable for the conversion of the pyrrolesulfonamide derivatives (I) into their salts can include inorganic acids such as hydrochloric acid, nitric acid, sulfuric acid, phosphoric acid and hydrobromic acid; and organic acids such as maleic acid, fumaric acid, tartaric acid, lactic acid, citric acid, acetic acid, methanesulfonic acid, p-toluenesulfonic acid, adipic acid, palmitic acid and tannic acid.

Further, the compounds (I) according to the present invention include those containing asymmetric centers. Each racemic mixture can be isolated by one or more of various methods, whereby a single optically-active substance can be obtained. Usable methods include, for example:

(1) Isolation by an optically active column.

(2) Isolation by recrystallization subsequent to conversion into a salt with an optically active acid.

(3) Isolation by an enzyme reaction.

(4) Isolation by a combination of the above methods (1) to (3).

The pyrrolesulfonamide derivatives (I) and their salts, which are obtained as described above, have strong serotonin-2 blocking action as will be demonstrated in tests to be described subsequently herein. Moreover, the compounds (I) according to the present invention have also been found to include those also having $\alpha_1$ blocking action. From the results of toxicity tests, the compounds (I) according to the present invention have also been found to possess high safety.

The compounds (I) according to the present invention can therefore be used as pharmaceuticals for the treatment of circulatory diseases such as ischemic heart diseases, cerebrovascular disturbances, peripheral circulatory disturbances and hypertension.

When the pyrrolesulfonamide derivatives (I) according to this invention are used as pharmaceuticals, they can be administered in an effective dose as they are. As an alternative, they can also be formulated into various preparation forms by known methods and then administered.

Exemplary preparation forms as medicines include orally administrable preparation forms such as tablets, powders, granules, capsules and syrups as well as parenterally administrable preparation forms such as injections and suppositories. Whichever preparation form is used, a known liquid or solid extender or carrier usable for the formulation of the preparation form can be employed.

Examples of such extender or carrier include polyvinylpyrrolidone, arabic gum, gelatin, sorbit, cyclodextrin, tragacanth gum, magnesium stearate, talc, polyethylene glycol, polyvinyl alcohol, silica, lactose, crystalline cellulose, sugar, starch, calcium phosphate, vegetable oil, carboxymethylcellulose, sodium laurylsulfate, water, ethanol, glycerin, mannitol, syrup, and the like.

When the compounds (I) according to the present invention are used as pharmaceuticals, their dose varies depending on the administration purpose, the age, body weight, conditions, etc. of the patient to be administered. In oral administration, the daily dose may generally be about 0.01–1,000 mg.

The present invention will next be described in further detail by the following referential examples, examples and tests. It is however to be noted that the present invention is by no means limited to the following examples.

REFERENTIAL EXAMPLE 1

Synthesis of sodium 3-pyrrolesulfonate (Compound 1)

A mixture consisting of 30.0 g (447 mmol) of pyrrole, 75.0 g (471 mmol) of sulfur trioxide-pyridine complex and 250 ml of 1,2-dichloroethane was refluxed for 16 hours. The top layer of the reaction mixture was removed by decantation. To the residue, 150 ml of water and 30 g of sodium carbonate were added successively. After the resulting mixture was boiled, the solvent was distilled off under reduced pressure. Ethanol-water (9:1 v/v, 500 ml) was added to the residue, followed by reflux for 1 hour. The reaction mixture was subjected to hot filtration, and the filtrate was allowed to cool down. Precipitated crystals were collected, washed with chilled ethanol and diethyl ether, and then dried under reduced pressure, whereby 17.0 g of powdery crystals were obtained.

REFERENTIAL EXAMPLE 2

Synthesis of benzyl 2-(3-pyrrolesulfonamide)acetate (Compound 2)

A suspension of 16.9 g (100 mmol) of Compound 1 and 22.9 g (110 mmol) of phosphorus pentachloride in 750 ml of diethyl ether was stirred at room temperature for 2 hours, and was then refluxed for 4 hours. After the reaction mixture was allowed to cooled down, it was filtered. The filtrate was washed successively with ice water (twice), a chilled, saturated aqueous solution of sodium hydrogencarbonate, ice water and a chilled, saturated aqueous solution of sodium chloride. The organic layer was dried over anhydrous sodium sulfate and then concentrated under reduced pressure, whereby 11.2 g of 3-pyrrolesulfonyl chloride were obtained as crude crystals.

After a mixture consisting of the whole amount of the thus-obtained crude crystals, 32.6 g (96.6 mmol) of glycine benzyl ester p-toluenesulfonate, 19.6 g (193 mmol) of triethylamine and 250 ml of tetrahydrofuran (hereinafter called "THF") was refluxed for 6 hours, the reaction mixture was concentrated under reduced pressure. Ethyl acetate was added to the residue. The resulting mixture was washed successively with a 10% aqueous solution of citric acid, water and a saturated aqueous solution of sodium chloride, dried over anhydrous sodium sulfate, and then concentrated under reduced pressure. The residue was treated with activated carbon under heat in methanol and then recrystallized from methanol, whereby 12.6 g of the title compound were obtained (yield: 43% based on sodium 3-pyrrolesulfonate).

REFERENTIAL EXAMPLE 3

Synthesis of benzyl 3-(3-pyrrolesulfonamide)propionate (Compound 3)

A mixture consisting of 1.66 g (10 mmol) of 3-pyrrolesulfonyl chloride obtained by the process of Referential Example 2, 7.03 g (20 mmol) of β-alanine benzyl ester p-toluenesulfonate, 4.05 g (40 mmol) of triethylamine and 100 ml of THF was refluxed for 16 hours. The reaction mixture was concentrated under reduced pressure, and ethyl acetate was added to the residue. The organic layer was washed successively with a saturated aqueous solution of sodium hydrogencarbonate, water, a 10% aqueous solution of citric acid, water and a saturated aqueous solution of sodium chloride, dried over anhydrous sodium sulfate, and then concentrated under reduced pressure. The residue was purified by column chromatography on silica gel (Merck & Co. Inc. No. 9385) (the same silica gel were used in the subsequent examples) (eluent: ethyl acetate/hexane=1/1), whereby 2.82 g of the title compound were obtained-(yield: 92%).

REFERENTIAL EXAMPLE 4

Synthesis of 2-(3-pyrrolesulfonamide)acetic acid (Compound 4)

To a solution of 4.85 g (16 mmol) of Compound 2 in 150 ml of THF, 480 mg of 10% palladium on charcoal were added, followed by stirring at room temperature for 15 hours under a hydrogen gas stream. The reaction mixture was filtered and the filtrate was concentrated under reduced pressure. The residue was recrystallized from acetonitrile, whereby 2.87 g of the title compound were obtained (yield: 88%).

REFERENTIAL EXAMPLE 5

Synthesis of 3-(3-pyrrolesulfonamide)propionic acid (Compound 5)

To a solution of 19.60 g (64 mmol) of Compound 3 in 400 ml of THF, 1.96 g of 5% palladium on charcoal were added, followed by stirring at room temperature for 4 hours under a hydrogen gas stream. The reaction mixture was filtered and the filtrate was concentrated under reduced pressure. The residue was recrystallized from ethyl acetate, whereby 11.96 g of the title compound were obtained (yield: 86%).

REFERENTIAL EXAMPLE 6

Synthesis of 2,3,4,5-tetrahydropyrrolo[2,3-e][1,2]thiazin-4-one 1,1-dioxide (Compound 6) and 2,3,4,6-tetrahydropyrrolo[3,4-e][1,2]thiazin-4-one 1,1-dioxide (Compound 7)

Under ice cooling, 5.00 g (24.5 mmol) of Compound 4, 4.27 ml (49 mmol) of oxalyl chloride, 120 ml of THF and 3 droplets of DMF were mixed, and the resulting mixture was stirred for 1 hour. The reaction mixture was concentrated under reduced pressure, and 120 ml of 1,2-dichloroethane were added to the residue. Under ice-cooled stirring, 6.53 g (49 mmol) of aluminum chloride were added, followed by stirring for 2.5 hours at the same temperature. Under ice cooling, 43 ml of 6 N hydrochloric acid were added. After the resultant mixture was saturated with sodium chloride, the thus-obtained mixture was extracted with THF (three times). The organic layer was washed with a saturated aqueous solution of sodium chloride, dried over anhydrous sodium sulfate, and then concentrated under reduced pressure. The residue was separated by chromatography on a silica gel column (eluent: ethyl acetate/hexane=1/1→2/1), whereby 2.27 g of Compound 6 and 62 mg of Compound 7 were obtained (yields: 50% and 1%, respectively).

REFERENTIAL EXAMPLE 7

Synthesis of 3,4,5,6-tetrahydro-2H-pyrrolo[2,3-f][1,2]thiazepin-5-one 1,1-dioxide (Compound 8) and 3,4,5,7-tetrahydro-2H-pyrrolo[3,4-f][1,2]thiazepin-5-one 1,1-dioxide (Compound 9)

A mixture consisting of 6.00 g (27.5 mmol) of Compound 5 and 300 g of polyphosphoric acid was stirred for 1 hour over an oil bath of 100° C. The reaction mixture was ice-cooled and was then poured into ice water. A concentrated aqueous solution of sodium hydroxide was added to adjust the pH to 4. Subsequent to saturation with sodium chloride, the resulting mixture was extracted with THF (3 times). The organic layer was washed with a saturated aqueous solution of sodium chloride, dried over anhydrous sodium sulfate, and then concentrated under reduced pressure. The residue was separated by chromatography on a silica gel column (eluent: ethyl acetate/hexane=2/1), whereby 2.50 g of Compound 8 and 497 mg of Compound 9 were obtained (yields: 46% and 9%, respectively).

EXAMPLE 1

Synthesis of sodium 1-methylpyrrole-3-sulfonate monohydrate (Compound 10)

Under an argon gas atmosphere, a solution of 9.44 g (50 mmol) of trimethylsilyl chlorosulfonate in 50 ml of carbon tetrachloride was gradually added under stirring to a solution of 18.5 g (50 mmol) of 1-methyl-2-tri-n-butylstannylpyrrole in 150 ml of carbon tetrachloride, followed by stirring at 50° C. for 30 minutes and further at room temperature for 30 minutes. To the reaction mixture, 300 ml of a saturated aqueous solution of sodium hydrogencarbonate were added, followed by stirring at room temperature for 20 minutes. The reaction mixture was allowed to separate into two layers. The water layer was collected and then washed with ethyl ether (100 ml×3 times). From the water layer, water was distilled off under reduced pressure, followed by the addition of ethanol to the residue. The resulting mixture was boiled and then subjected to hot filtration. The solvent in the filtrate was distilled off under reduced pressure, and the thus-obtained solid was washed with n-pentane (200 ml×2 times) and then dried under reduced pressure. Colorless powdery crystals (6.67 g) were obtained.

EXAMPLE 2

Synthesis of sodium 1-methylpyrrole-3-sulfonate monohydrate (Compound 10) (alternative process)

A mixture consisting of 48.3 g (595 mmol) of 1-methylpyrrole, 100 g (628 mmol) of sulfur trioxide-pyridine complex and 325 ml of 1,2-dichloroethane was refluxed for 24 hours. The top layer of the reaction mixture was removed by decantation, and 225 ml of water and 100 g of sodium carbonate were successively added to the residue. The resulting mixture was boiled, and the solvent was distilled off under reduced pressure. Ethanol-water (9:1 v/v, 1167 ml) was added to the residue. The thus-obtained mixture was refluxed for 30 minutes and was then subjected to hot filtration. The filtrate was concentrated under reduced pressure and the residue was recrystallized from water-ethanol, whereby 7.05 g of powdery crystals were obtained.

EXAMPLE 3

Synthesis of benzyl 2-[3-(1-methylpyrrole)sulfonamide]propionate (Compound 11)

A suspension of 7.40 g (36.8 mmol) of the sodium 1-methylpyrrole-3-sulfonate monohydrate obtained in Example 1 and 9.25 g (44.4 mmol) of phosphorus pentoxide in 303 ml of diethyl ether was stirred at room temperature for 2 hours. The reaction mixture was filtered, and the filtrate was washed successively with chilled water, a chilled, half-saturated aqueous solution of sodium hydrogencarbonate, chilled water and a chilled, saturated aqueous solution of sodium chloride. The organic layer was dried over anhydrous sodium sulfate and then concentrated under reduced pressure, whereby 4.14 g of 3-(1-methylpyrrole)sulfonyl chloride were obtained as crude crystals.

After a mixture consisting of the whole amount of the thus-obtained crude crystals, 12.18 g (34.65 mmol) of β-alanine benzyl ester p-toluenesulfonate, 7.01 g (69.3 mmol) of triethylamine and 200 ml of THF was refluxed for 17 hours, the reaction mixture was allowed to cool down and was then filtered. The filtrate was concentrated under reduced pressure. Ethyl acetate was added to the residue. The resulting mixture was washed successively with water, a 10% aqueous solution of citric acid, water and a saturatred aqueous solution of sodium chloride, dried over anhydrous sodium sulfate, and then concentrated under reduced pressure. The residue was purified by chromatography on a silica gel column (eluent: ethyl acetate/hexane=1/1), whereby 5.97 g of the title compound were obtained (yield: 50%).

EXAMPLE 4

Synthesis of
3-[3-(1-methylpyrrole)sulfonamide]propionic acid
(Compound 12)

To a solution of 5.595 g (17.36 mmol) of Compound 11 in 200 ml of THF, 560 mg of 5% palladium on charcoal were added, followed by stirring at room temperature for 24 hours under a hydrogen gas stream. The reaction mixture was filtered and the filtrate was concentrated under reduced pressure. The residue was recrystallized from 2-propanol-diisopropyl ether, whereby 3.49 g of the title compound were obtained (yield: 81%).

EXAMPLE 5

Synthesis of 5-methyl-2,3,4,5-tetrahydropyrrolo[2,3-e][1,2]thiazin-4-one 1,1-dioxide (Compound 13)

A suspension of 2.06 g (14 mmol) of Compound 6, 1.3 ml (14 mmol) of dimethyl sulfate, 1.90 g (14 mmol) of potassium carbonate in 140 ml of acetone was stirred at room temperature for 5 hours. The reaction mixture was filtered, and the filtrate was concentrated under reduced pressure. The residue was purified by chromatography on a silica gel column (eluent: THF/methylene chloride=1/7), whereby 2.40 g of the title compound were obtained (yield: 86%).

EXAMPLE 6

Synthesis of 6-methyl-3,4,5,6-tetrahydro-2H-pyrrolo[2,3-f][1,2]thiazepin-5-one 1,1-dioxide (Compound 14)

A suspension of 200 mg (1 mmol) of Compound 8, 126 mg (1 mmol) of dimethyl sulfate and 138 mg (1 mmol) of potassium carbonate in 20 ml of acetone was refluxed for 12 hours. The reaction mixture was concentrated under reduced pressure, followed by the addition of a saturated aqueous solution of sodium chloride to the residue. The resultant mixture was extracted with chloroform (3 times). The organic layer was dried over anhydrous sodium sulfate and then concentrated under reduced pressure. The residue was purified by chromatography on a silica gel column (eluent: methanol/chloroform=1/19), whereby 135 mg of the title compound were obtained (yield: 63%).

EXAMPLE 7

Synthesis of 7-methyl-3,4,5,7-tetrahydro-2H-pyrrolo[3,4-f][1,2]thiazepin-5-one 1,1-dioxide (Compound 15)

A suspension of 480 mg (2.4 mmol) of Compound 9, 303 mg (2.4 mmol) of dimethyl sulfate and 332 mg (2.4 mmol) of potassium carbonate in 50 ml of acetone was stirred at room temperature for 22 hours. The reaction mixture was concentrated under reduced pressure, and water and 1 g of citric acid were added to the residue. The thus-obtained mixture was extracted with chloroform (3 times). The organic layer was washed with a saturated aqueous solution of sodium chloride, dried over anhydrous sodium sulfate, and then concentrated under reduced pressure. The residue was purified by chromatography on a silica gel column (eluent: methanol/chloroform=1/19), whereby 347 mg of the title compound were obtained (yield: 68%).

EXAMPLE 8

Synthesis of 7-methyl-3,4,5,7-tetrahydro-2H-pyrrolo[3,4-f][1,2]thiazepin-5-one 1,1-dioxide (Compound 15) (alternative process)

A mixture consisting of 497 mg (2 mmol) of Compound 12 and 25 g of polyphosphoric acid was stirred for 1 hour over an oil bath of 100° C. The reaction mixture was added to about 200 ml of ice water, and potassium carbonate was added to adjust the pH to 4. Subsequent to saturation with sodium chloride, the resultant mixture was extracted with chloroform (3 times). The organic layer was washed with water and a saturated aqueous solution of sodium chloride, dried over anhydrous sodium sulfate, and then concentrated under reduced pressure. The residue was purified by chromatography on a silica gel column (eluent: ethyl acetate), whereby 80 mg of the title compound were obtained (yield: 17%).

EXAMPLE 9

Synthesis of 2-(3-chloropropyl)-5-methyl-2,3,4,5-tetrahydropyrrolo[2,3-e][1,2]thiazin-4-one 1,1-dioxide (Compound 16)

A suspension of 200 mg (1 mmol) of Compound 13, 189 mg (1.2 mmol) of 1-bromo-3-chloropropane and 345 mg (2.5 mmol) of potassium carbonate in 5 ml of acetone was refluxed for 6 hours. The reaction mixture was filtered, and the filtrate was concentrated under reduced pressure. The residue was purified by chromatography on a silica gel column (eluent: ethyl acetate/methylene chloride=1/30), whereby 125 mg of the title compound were obtained (yield: 45%).

EXAMPLE 10

Synthesis of 2-(3-bromopropyl)-5-methyl-2,3,4,5-tetrahydropyrrolo[2,3-e][1,2]thiazin-4-one 1,1-dioxide (Compound 17)

A suspension of 500 mg (2.5 mmol) of Compound 13, 2.5 g (12.5 mmol) of 1,3-dibromopropane and 690 mg (5 mmol) of potassium carbonate in 25 ml of acetone was refluxed for 12 hours. The reaction mixture was filtered, and the filtrate was concentrated under reduced pressure. The residue was purified by chromatography on a silica gel column (eluent: ethyl acetate/methylene chloride=1/40), whereby 274 mg of the title compound were obtained (yield: 34%).

EXAMPLE 11

Synthesis of 2-(3-chloropropyl)-6-methyl-3,4,5,6-tetrahydro-2H-pyrrolo[2,3-f][1,2]thiazepin-5-one 1,1-dioxide (Compound 18)

A suspension of 214 mg (1 mmol) of Compound 14, 630 mg (4 mmol) of 1-bromo-3-chloropropane and 276 mg (2 mmol) of potassium carbonate in 5 ml of acetone was refluxed for 6 hours. The reaction mixture was filtered, and the filtrate was concentrated under reduced pressure. The residue was purified by chromatography on a silica gel column (eluent: ethyl acetate/hexane=1/2), whereby 275 mg of the title compound were obtained (yield: 95%).

EXAMPLE 12

Synthesis of 2-(3-chloropropyl)-4-hydroxyimino-5-methyl-2,3,4,5-tetrahydropyrrolo[2,3-e][1,2]thiazine 1,1-dioxide (Compound 19)

A suspension of 300 mg (1.08 mmol) of Compound 16, 113 mg (1.62 mmol) of hydroxylamine hydrochloride and 159 mg (1.62 mmol) of potassium acetate in 10 ml of methanol was refluxed for 7 hours. To the reaction mixture, 75 mg (1.08 mmol) of hydroxylamine hydrochloride and 106 mg (1.08 mmol) of potassium acetate were added, followed by further refluxing for 13 hours. Post treatment and purification were conducted as in Example 9, whereby 277 mg of the title compound were obtained (yield: 88%).

EXAMPLE 13

Synthesis of 2-(3-chloropropyl)-5-hydroxyimino-6-methyl-3,4,5,6-tetrahydro-2H-pyrrolo[2,3-f][1,2]thiazepine 1,1-dioxide (Compound 20)

A suspension of 404 mg (1.39 mmol) of Compound 18, 290 mg (4.17 mmol) of hydroxylamine hydrochloride and 342 mg (4.17 mmol) of sodium acetate in 40 ml of methanol was refluxed for 22 hours. To the reaction mixture, 97 mg (1.39 mmol) of hydroxylamine hydrochloride and 114 mg (1.39 mmol) of sodium acetate were added, followed by further refluxing for 19 hours. The reaction mixture was concentrated under reduced pressure and a half-saturated aqueous solution of potassium carbonate was added to the residue. The thus-obtained mixture was extracted with chloroform (3 times). The organic layer was washed successively with water and a saturated aqueous solution of sodium chloride, dried over anhydrous sodium sulfate, and then concentrated under reduced pressure. The residue was purified by chromatography on a silica gel column (eluent: chloroform), whereby 338 mg of the title compound were obtained (yield: 80%).

EXAMPLE 14

Synthesis of 2-[3-[4-(4-fluorophenyl)piperazin-1-yl]propyl]-5-methyl-2,3,4,5-tetrahydropyrrolo[2,3-e][1,2]thiazin-4-one 1,1-dioxide (Compound 21)

A suspension of 54 mg (0.17 mmol) of Compound 17, 46 mg (0.25 mmol) of 1-(4-fluorophenyl)piperazine and 57 mg (0.68 mmol) of sodium hydrogencarbonate in 3.4 ml of dioxane was refluxed for 7 hours. Post treatment and purification were conducted as in Example 9, whereby 67 mg of the title compound were obtained (yield: 94%).

EXAMPLE 15

Synthesis of 2-[3-[4-(4-fluorobenzoyl)piperidino]propyl]-6-methyl-3,4,5,6-tetrahydro-2H-pyrrolo[2,3-f][1,2]thiazepin-5-one 1,1-dioxide (Compound 22)

A suspension of 116 mg (0.4 mmol) of Compound 18, 97 mg (0.4 mmol) of 4-(4-fluorobenzoyl)piperidine hydrochloride, 134 mg (1.6 mmol) of sodium hydrogencarbonate and 120 mg (0.8 mmol) of sodium iodide in 5 ml of acetonitrile was refluxed for 17 hours. Post treatment was conducted as in Example 13, and the residue was purified by chromatography on a silica gel column (eluent: methanol/chloroform=3/97), whereby 137 mg of the title compound were obtained (yield: 74%).

EXAMPLE 16

Synthesis of 2-[3-[4-(4-fluorophenyl)piperazin-1-yl]propyl]-6-methyl-3,4,5,6-tetrahydro-2H-pyrrolo[2,3-f][1,2]thiazepin-5-one 1,1-dioxide (Compound 23)

A suspension of 116 mg (0.4 mmol) of Compound 18, 108 mg (0.6 mmol) of 1-(4-fluorophenyl)piperazine, 83 mg (0.6 mmol) of potassium carbonate and 120 mg (0.8 mmol) of sodium iodide in 6 ml of acetonitrile was refluxed for 19 hours. The reaction mixture was concentrated under reduced pressure, a half-saturated aqueous solution of potassium carbonate was added to the residue, and the resultant mixture was extracted with ethyl acetate. The organic layer was washed successively with water and a saturated aqueous solution of sodium chloride, dried over anhydrous sodium sulfate, and then concentrated under reduced pressure. The residue was purified by chromatography on a silica gel column (eluent: methanol/chloroform=3/97), whereby 173 mg of the title compound were obtained (yield: 100%).

EXAMPLE 17

Synthesis of 2-[3-[4-(4-fluorophenyl)piperazin-1-yl]propyl]-7-methyl-3,4,5,7-tetrahydro-2H-pyrrolo[3,4-f][1,2]thiazepin-5-one 1,1-dioxide (Compound 24)

A suspension of 236 mg (1.1 mmol) of Compound 15, 308 mg (1.2 mmol) of 1-(3-chloropropyl)-4-(4-fluorophenyl)piperazine and 304 mg (2.2 mmol) of potassium carbonate in 15 ml of 2-butanone was refluxed for 16 hours. The reaction mixture was filtered, and the filtrate was concentrated under reduced pressure. The residue was purified by chromatography on a silica gel column (eluent: ethyl acetate), whereby 276 mg of the title compound were obtained (yield: 58%).

EXAMPLE 18

Synthesis of 2-[3-[4-(4-fluorophenyl)piperazin-1-yl]propyl]-4-hydroxyimino-5-methyl-2,3,4,5-tetrahydropyrrolo[2,3-e][1,2]thiazine 1,1-dioxide (Compound 25)

A suspension of 116 mg (0.4 mmol) of Compound 19, 108 mg (0.6 mmol) of 1-(4-fluorophenyl)piperazine, 134 mg (1.6 mmol) of sodium hydrogencarbonate and 120 mg (0.8 mmol) of sodium iodide in 8 ml of acetonitrile was refluxed for 23 hours. The reaction mixture was filtered, and the filtrate was concentrated under reduced pressure. The residue was purified by chromatography on a silica gel column (eluent: methanol/methylene chloride=1/20), whereby 152 mg of the title compound were obtained (yield: 87%).

EXAMPLE 19

Synthesis of 2-[3-[4-(4-fluorobenzoyl)piperidino]propyl]-4-hydroxyimino-5-methyl-2,3,4,5-tetrahydropyrrolo[2,3-e][1,2]thiazine 1,1-dioxide (Compound 26)

A suspension of 116 mg (0.4 mmol) of Compound 19, 389 mg (0.6 mmol) of 4-(4-fluorobenzoyl)piperidine hydrochloride, 134 mg (1.6 mmol) of sodium hydrogencarbonate and 120 mg (0.8 mmol) of sodium iodide in 8 ml of acetonitrile was refluxed for 24 hours. The reaction mixture was filtered, and the filtrate was concentrated under reduced pressure.

The residue was purified by chromatography on a silica gel column (eluent: methanol/methylene chloride=1/15), whereby 90 mg of the title compound were obtained (yield: 49%).

EXAMPLE 20

Synthesis of 2-[3-[4-(4-fluorophenyl)piperazin-1-yl]propyl]-5-hydroxyimino-6-methyl-3,4,5,6-tetrahydro-2H-pyrrolo[2,3-f][1,2]thiazepine 1,1-dioxide (Compound 27)

A suspension of 112 mg (0.4 mmol) of Compound 20, 108 mg (0.6 mmol) of 1-(4-fluorophenyl)piperazine, 83 mg (0.6 mmol) of potassium carbonate and 120 mg (0.8 mmol) of sodium iodide in 6 ml of acetonitrile was refluxed for 18 hours. The reaction mixture was concentrated under reduced pressure, and a half-saturated aqueous solution of potassium carbonate was added to the residue. The water layer was saturated with sodium chloride, and the thus-obtained mixture was extracted with THF. The organic layer was dried over anhydrous sodium sulfate and then concentrated under reduced pressure. The residue was purified by chromatography on a silica gel column (eluent: methanol/chloroform=3/97), whereby 53 mg of the title compound were obtained (yield: 29%).

EXAMPLE 21

Synthesis of 2-[3-[4-(4-fluorobenzoyl)piperidino]propyl]-5-hydroxyimino-6-methyl-3,4,5,6-tetrahydro-2H-pyrrolo[2,3-f][1,2]thiazepine 1,1-dioxide (Compound 28)

A suspension of 112 mg (0.4 mmol) of Compound 20, 97 mg (0.4 mmol) of 4-(4-fluorobenzoyl)piperidine hydrochloride, 134 mg (1.6 mmol) of sodium hydrogencarbonate and 120 mg (0.8 mmol) of sodium iodide in 5 ml of acetonitrile was refluxed for 14 hours. Post treatment and purification were conducted as in Example 15, whereby 181 mg of the title compound were obtained (yield: 95%).

EXAMPLE 22

Synthesis of 2-[3-[4-(4-fluorophenyl)piperazin-1-yl]propyl]-4-hydroxy-5-methyl-2,3,4,5-tetrahydropyrrolo[2,3-e][1,2]thiazine 1,1-dioxide (Compound 29)

To a suspension of 42 mg (0.1 mmol) of Compound 21 in 5 ml of ethanol, 38 mg (1 mmol) of sodium borohydride were added gradually under ice-cooled stirring. The resulting mixture was stirred under ice cooling for 1 hour and further at room temperature for 13 hours. Water (5 ml) was added to the reaction mixture. The thus-obtained mixture was stirred at room temperature for 5 hours and then concentrated under reduced pressure. Post treatment and purification were conducted as in Example 15, whereby 36 mg of the title compound were obtained (yield: 85%).

EXAMPLE 23

Synthesis of 2-[3-[4-(4-fluorophenyl)piperazin-1-yl]propyl]-5-hydroxy-6-methyl-3,4,5,6-tetrahydro-2H-pyrrolo[2,3-f][1,2]thiazepine 1,1-dioxide (Compound 30)

To a suspension of 240 mg (0.57 mmol) of Compound 23 in 5 ml of ethanol, 200 mg (5.3 mmol) of sodium borohydride were added gradually under ice-cooled stirring. The resulting mixture was stirred under ice cooling for 1 hour and further at room temperature for 4 hours. A saturated aqueous solution of ammonium chloride was added to the reaction mixture under ice cooling, followed by the addition of a saturated aqueous solution of sodium hydrogencarbonate so that the mixture was alkalinized. The water layer was extracted with methylene chloride. The organic layer was dried over anhydrous magnesium sulfate and then concentrated under reduced pressure. The residue was purified by chromatography on a silica gel column (eluent: methanol/methylene chloride=1/20), whereby 186 mg of the title compound were obtained (yield: 77%).

EXAMPLE 24

Synthesis of 2-[3-[4-(4-fluorophenyl)piperazin-1-yl]propyl]-5-hydroxy-7-methyl-3,4,5,7-tetrahydro-2H-pyrrolo[3,4-f][1,2]thiazepine 1,1-dioxide (Compound 31)

To a suspension of 174 mg (0.4 mmol) of Compound 24 in 8 ml of ethanol, 151 mg (4 mmol) of sodium borohydride were added gradually under ice-cooled stirring. The resulting mixture was stirred under ice cooling for 1 hour and further at room temperature for 13 hours. Water (80 ml) was added to the reaction mixture. The thus-obtained mixture was stirred at room temperature for 30 minutes and then concentrated under reduced pressure. Post treatment and purification were conducted as in Example 15, whereby 151 mg of the title compound were obtained (yield: 86%).

Physical data of the compounds obtained in Examples 1–24 are shown in Tables 1–6.

TABLE 1

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 10 | 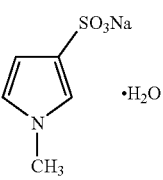 | Colorless powdery crystals ≧250° C. | (400MHz)(D$_2$O/TSP-d$_4$**) 3.67(3H, s), 6.37(1H, s), 6.75(1H, s), 7.11(1H, s) | (KBr) 3446, 3132, 1636, 1526, 1186, 1148, 1060, 1048, 942, 802, 699, 662 |

TABLE 1-continued

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 11 | (pyrrole with N-CH$_3$, S(O$_2$)-NH-CH$_2$CH$_2$-COOBzl) | Colorless oil | (400MHz) 2.60(2H, t, J=6.2Hz), 3.23(2H, m), 3.66(3H, s), 4.93(1H, br. t), 6.38(1H, m), 6.59(1H, m), 7.11(1H, m), 7.28–7.41(5H, m) | (film) 3283, 1732, 1519, 1323, 1155, 1119, 801, 699 |
| 12 | (pyrrole with N-CH$_3$, S(O$_2$)-NH-CH$_2$CH$_2$-COOH) | Pale yellow powdery crystals 95.5–98.0° C. (isopropanol-isopropyl ether) | (400MHz)(DMSO-d$_6$/TMS) 2.37(2H, t, J=7.2Hz), 2.92(2H, m), 3.66(3H, s), 6.27(1H, m), 6.83(1H, m), 6.99(1H, br), 7.25(1H, m), 12.18(1H, br) | (KBr) 3281, 1718, 1522, 1422, 1310, 1241, 1150, 1040, 801, 688 |

*Measured in CDCl$_3$ with TMS as an internal standard unless otherwise specifically indicated.

**TSP-d$_4$ = sodium 3-(trimethylsilyl)propionate-d$_4$

TABLE 2

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 13 | (fused pyrrole-thiazinone, N-CH$_3$) | Colorless powdery crystals 142.0–143.0° C. (ethyl acetate-hexane) | (270MHz) 3.98(3H, s), 4.16(2H, d, J=7.3Hz), 5.30(1H, t, J=7.3Hz), 6.55(1H, d, J=2.6Hz), 6.91(1H, d, J=2.6Hz) | (KBr) 3196, 1673, 1648, 1382, 1328, 1307, 1209, 1162, 1142, 1083, 762 |
| 14 | (fused pyrrole-thiazepinone, N-CH$_3$) | Colorless prism crystals 132.0–133.5° C. (chloroform) | (270MHz)(DMSO-d$_6$/TMS) 3.01(2H, m), 3.33(2H, m), 3.82(3H, s), 6.52(1H, d, J=2.6Hz), 7.22(1H, d, J=2.6Hz), 7.86(1H, t, J=5.6Hz) | (KBr) 3303, 1652, 1481, 1403, 1321, 1200, 1151, 1094, 1018, 983, 866, 783, 766, 674 |
| 15 | (fused pyrrole-thiazepinone, H$_3$C-N) | Pale yellow prism crystals 135.0–138.0° C. (ethyl acetate-isopropyl ether) | (400MHz)(DMSO-d$_6$/TMS) 2.83(2H, m), 3.38(2H, m), 3.68(3H, s), 7.43(1H, d, J=2.4Hz), 7.45(1H, d, J=2.4Hz), 7.75(1H, br. s.) | (KBr) 3235, 1642, 1538, 1322, 1242, 1153, 1050, 858, 755 |
| 16 | (fused pyrrole-thiazinone with N-(CH$_2$)$_3$Cl, N-CH$_3$) | Colorless prism crystals 96.0–97.0° C. (ethyl acetate-hexane) | (270MHz) 2.08(2H, quint, J=6.6Hz), 3.35(2H, t, J=6.6Hz), 3.65(2H, t, J=6.6Hz), 3.99(3H, s), 4.22(2H, s), 6.53(1H, d, J=2.6Hz), 6.92(1H, d, J=2.6Hz) | (KBr) 1680, 1387, 1326, 1210, 1150, 1011, 900, 774, 705 |

*Measured in CDCl$_3$ with TMS as an internal standard unless otherwise specifically indicated.

TABLE 3

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 17 | [structure with (CH$_2$)$_3$Br substituent, pyrrole fused with sulfonyl ring, N-CH$_3$, C=O] | Colorless prism crystals 84.0–85.0° C. (ethyl acetate-hexane) | (270MHz) 2.16(2H, quint., J=6.6Hz), 3.34(2H, t, J=6.6Hz), 3.50(2H, t, J=6.6Hz), 3.99(3H, s), 4.23(2H, s), 6.53(1H, d, J=2.6Hz), 6.91(1H, d, J=2.6Hz) | (KBr) 1680, 1484, 1389, 1328, 1260, 1212, 1149, 1006, 898, 715 |
| 18 | [structure with (CH$_2$)$_3$Cl substituent, seven-membered ring, N-CH$_3$, C=O] | Colorless needle crystals 71.0–74.0° C. (ethyl acetate-hexane) | (270MHz) 2.04(2H, quint., J=6.6Hz), 3.17(2H, t, J=6.6Hz), 3.25(2H, m), 3.53–3.67(4H, m), 3.92(3H, s), 6.66(1H, d, J=2.6Hz), 6.81(1H, d, J=2.6Hz) | (KBr) 3120, 2964, 1661, 1472, 1405, 1375, 1330, 1213, 1196, 1152, 1096, 1026, 964, 854, 757, 707 |
| 19 | [structure with (CH$_2$)$_3$Cl substituent, N-CH$_3$, =NOH] | Colorless prism crystals 126.0–127.0° C. (ethyl acetate-hexane) | (270MHz) 2.09(2H, quint., J=6.6Hz), 3.17(2H, t, J=6.6Hz), 3.67(2H, t, J=6.6Hz), 3.84(3H, s), 4.64(2H, s), 6.48(1H, d, J=2.6Hz), 6.71(1H, d, J=2.6Hz), 7.53(1H, s) | (KBr) 3465, 1610, 1483, 1365, 1298, 1207, 1148, 1023, 994, 936, 848, 795 |
| 20 | [structure with (CH$_2$)$_3$Cl substituent, seven-membered ring, N-CH$_3$, =NOH] | Colorless prism crystals 110.0–111.0° C. (ethyl acetate-hexane) | (400MHz) 2.04(2H, quint., J=6.4Hz), 3.15–3.21(4H, m), 3.60–3.66(4H, m), 3.73(3H, s), 6.57(1H, d, J=2.9Hz), 6.60(1H, d, J=2.9Hz), 7.59(1H, s) | (KBr) 3358, 3120, 2949, 1486, 1413, 1308, 1194, 1142, 1062, 988, 953, 936, 907, 870, 757, 730, 707 |

*Measured in CDCl$_3$ with TMS as an internal standard unless otherwise specifically indicated.

TABLE 4

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 21 | [structure with (CH$_2$)$_3$-piperazine-C$_6$H$_4$-F substituent] | Colorless needle crystals 141.0–142.0° C. (ethyl acetate-hexane) | (270MHz) 1.81(2H, quint., J=7.3Hz), 2.47(2H, t, J=7.3Hz), 2.58(4H, m), 3.11(4H, m), 3.27(2H, t, J=7.3Hz), 3.98(3H, s), 4.23(2H, s), 6.52(1H, d, J=2.6Hz), 6.84–6.99(5H, m) | (KBr) 2950, 2833, 1684, 1510, 1386, 1335, 1238, 1155, 1005, 900, 815, 782, 719 |
| 22 | [structure with (CH$_2$)$_3$-piperidine-C(=O)-C$_6$H$_4$-F substituent] | Colorless powdery crystals 105.0–107.0° C. (ethyl acetate-hexane) | (270MHz) 1.69–1.89(6H, m), 2.06(2H, m), 2.41(2H, m), 2.95(2H, m), 3.06(2H, t, J=7.3Hz), 3.18(1H, m), 3.24(2H, m), 3.56(2H, m), 3.92(3H, s), 6.65(1H, d, J=2.6Hz), 6.80(1H, d, J=2.6Hz), 7.14(2H, m), 7.96(2H, m) | (KBr) 2948, 2778, 1726, 1668, 1596, 1508, 1464, 1405, 1375, 1322, 1228, 1146, 1046, 980, 856, 755 |

TABLE 4-continued

| Comp'd No. | Structural formula | Property m.p. (recryst'n solvent) | NMR (δ ppm)* ( ): observation frequency | IR (cm⁻¹) ( ): measuring method |
|---|---|---|---|---|
| 23 | | Colorless powdery crystals 72.0–73.5° C. (ethyl acetate-hexane) | (270MHz) 1.77(2H, quint., J=7.3Hz), 2.44(2H, t, J=7.3Hz), 2.57(4H, m), 3.03–3.14(6H, m), 3.25(2H, m), 3.56(2H, m), 3.92(3H, s), 6.65(1H, d, J=2.6Hz), 6.80(1H, d, J=2.6Hz), 6.87(2H, m), 6.95(2H, m) | (KBr) 3609, 3128, 2842, 1661, 1508, 1452, 1404, 1386, 1318, 1247, 1216, 1143, 1038, 1014, 980, 958, 930, 846, 828, 780, 710 |
| 24 | | Colorless oil | (400MHz) 1.81(2H, quint., J=7.0Hz), 2.46(2H, t, J=7.0Hz), 2.58(4H, m), 3.05(2H, m), 3.10(4H, m), 3.16(2H, t, J=7.0Hz), 3.68(2H, m), 3.71(3H, s), 6.86(2H, m), 6.95(2H, m), 7.14(1H, d, J=2.5Hz), 7.25(1H, d, J=2.5Hz) | (film) 3124, 2945, 2819, 1655, 1531, 1509, 1456, 1329, 1232, 1156, 1038, 959, 827, 717 |

*Measured in CDCl₃ with TMS as an internal standard unless otherwise specifically indicated.

TABLE 5

| Comp'd No. | Structural formula | Property m.p. (recryst'n solvent) | NMR (δ ppm)* ( ): observation frequency | IR (cm⁻¹) ( ): measuring method |
|---|---|---|---|---|
| 25 | | Colorless needle crystals 177.0–178.0° C. (ethanol) | (270MHz)(DMSO-d₆/TMS) 1.71(2H, m), 2.38(2H, t, J=6.6Hz), 2.47(4H, m), 2.94(2H, t, J=6.6Hz), 3.05(4H, m), 3.83(3H, s), 4.51(2H, s), 6.42(1H, d, J=3.3Hz), 6.93(2H, m), 7.02(2H, m), 7.06(1H, d, J=3.3Hz), 11.89(1H, s) | (KBr) 2833, 1513, 1332, 1244, 1203, 1156, 950, 824, 725, 695 |
| 26 | | Colorless needle crystals 209.0–210.0° C. (decomp'd) (ethanol) | (270MHz)(DMSO-d₆/TMS) 1.56(2H, m), 2.64–2.78(4H, m), 2.04(2H, m), 2.33(2H, m), 2.85–2.95(4H, m), 3.35(1H, m), 3.84(3H, s), 4.49(2H, s), 6.42(1H, d, J=3.3Hz), 7.08(1H, d, J=3.3Hz), 7.34(2H, m), 8.04(2H, m), 11.89(1H, s) | (KBr) 2953, 1684, 1598, 1508, 1412, 1330, 1206, 1157, 973, 942, 837, 778, 739, 721 |
| 27 | | Colorless powdery crystals 237.0–239.0° C. (acetonitrile-isopropyl ether) | (400MHz)(DMSO-d₆/TMS) 1.69(2H, quint., J=6.9Hz), 2.33(2H, m), 2.48(4H, m), 2.93(2H, m), 2.99(2H, t, J=6.9Hz), 3.05(4H, m), 3.55(2H, m), 3.67(3H, s), 6.37(1H, d, J=2.9Hz), 6.89(1H, d, J=2.9Hz), 6.92(2H, m), 7.02(2H, m), 11.78(1H, s) | (KBr) 2960, 2824, 1509, 1448, 1323, 1245, 1231, 1195, 1150, 1040, 993, 995, 924, 816, 757, 728, 706 |

TABLE 5-continued

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 28 | (structure with O$_2$S-N, (CH$_2$)$_3$N-piperidine-C(=O)-C$_6$H$_4$-F, pyrrole fused ring with N-CH$_3$ and =NOH) | Colorless powdery crystals 192.5–195.0° C. (ethyl acetate-hexane) | (400MHz) 1.72–1.96(6H, m), 2.14(2H, m), 2.46(2H, m), 2.99–3.08(4H, m), 3.16–3.28(3H, m), 3.55(2H, m), 3.75(3H, s), 6.56(1H, d, J=3.0Hz), 6.59(1H, d, J=3.0Hz), 7.14(2H, m), 7.95(2H, m), 10.13(1H, br. s) | (KBr) 3402, 2953, 1680, 1597, 1505, 1450, 1412, 1327, 1196, 1150, 993, 973, 855, 726, 700 |

*Measured in CDCl$_3$ with TMS as an internal standard unless otherwise specifically indicated.

TABLE 6

| Comp'd No. | Structural formula | Property m.p. (recryst'n solvent) | NMR (δ ppm)* ( ): observation frequency | IR (cm$^{-1}$) ( ): measuring method |
|---|---|---|---|---|
| 29 | (structure with O$_2$S-N, (CH$_2$)$_3$N-piperazine-C$_6$H$_4$-F, pyrrole fused ring with N-CH$_3$ and OH) | Colorless powdery crystals 157.5–161.5° C. (ethyl acetate-hexane) | (400MHz) 1.83(2H, m), 2.35(2H, m), 2.46(1H, m), 2.61(2H, m), 2.70(1H, m), 2.82(2H, m), 2.95–3.05(3H, m), 3.52(1H, dd, J=2.0Hz, 14.8Hz), 3.63(3H, s), 3.92(1H, m), 4.20(1H, dd, J=2.8Hz, 14.8Hz), 4.52(1H, t, J=2.3Hz), 6.44(1H, d, J=3.0Hz), 6.60(1H, d, J=3.0Hz), 6.79(2H, m), 6.94(2H, m) | (KBr) 3528, 2953, 2820, 2360, 1510, 1464, 1310, 1232, 1209, 1140, 1059, 1003, 958, 920, 815, 776, 738, 713 |
| 30 | (structure with O$_2$S-N, (CH$_2$)$_3$N-piperazine-C$_6$H$_4$-F, pyrrole fused ring with N-CH$_3$ and OH, seven-membered ring) | Colorless oil | (270MHz) 1.82(2H, quint., J=7.3Hz), 1.93(1H, m), 2.14(1H, m), 2.40(1H, m), 2.49–2.65(5H, m), 2.78(1H, m), 3.10(4H, m), 2.25–2.38(2H, m), 3.67(3H, s), 4.40(1H, m), 4.92(1H, m), 6.43–6.45(2H, m), 6.87(2H, m), 6.95(2H, m) | (film) 3500, 2822, 1731, 1505, 1456, 1232, 1138, 930, 818, 706 |
| 31 | (structure with O$_2$S-N, (CH$_2$)$_3$N-piperazine-C$_6$H$_4$-F, pyrrole fused ring with H$_3$C-N and OH) | Colorless plate crystals 165.5–169.0° C. (ethyl acetate-hexane) | (400MHz) 1.81(2H, quint., J=7.1Hz), 1.92(2H, m), 2.47(2H, m), 2.59(4H, m), 2.83(1H, m), 3.05–4.05(6H, m), 3.44(1H, m), 3.62(3H, s), 4.12(1H, m), 4.87(1H, br. s), 6.56(1H, d, J=2.4Hz), 6.87(2H, m), 6.95(2H, m), 7.02(1H, d, J=2.4Hz) | (KBr) 3122, 2959, 2828, 1509, 1448, 1328, 1247, 1151, 1124, 1062, 1009, 928, 897, 830, 780, 758, 711, 692 |

*Measured in CDCl$_3$ with TMS as an internal standard unless otherwise specifically indicated.

Tests

With respect to certain compounds of the present invention, their anti-serotonin (5-HT) action and anti-$\alpha_1$ action were investigated by the methods which will be described below. The results of some representative compounds are shown in Table 7.

(1) Anti-Serotonin (5-HT) Action

The superior mesenteric artery of each Hartley male guinea pig (body weight: 300–500 g) was excised. A preparation cut in a helical form was suspended under resting-tension of 0.3 g in a Magnus cylinder filled with the Tyrode solution which had been aerated with a gas mixture of 95% $O_2$ and 5% $CO_2$ and maintained at 37° C. Using an isometric transducer ("UL-10", manufactured by SHINKOH K. K.) and a pressure preamplifier ("DSA-605A", manufactured by SHINKOH K. K.), variations in tension were measured. The isometric tensions were recorded on a pen-writing recorder ("VP-6537A", manufactured by NATIONAL K. K.). Taking the contraction induced by $10^{-5}$ M serotonin (5-HT) as 100%, the percent contractions by $10^{-5}$ M 5-HT in the presence of each test drug at $10^{-7}$ M and $10^{-6}$ M were determined as anti-5-HT action.

(2) Anti-α₁ Action

The thoracic aorta of each Hartley male guinea pig (body weight: 300–500 g) was excised. A preparation cut in a helical form was suspended under 1 g load in a Magnus cylinder filled with the Tyrode solution which had been aerated with a gas mixture of 95% O₂ and 5% CO₂ and maintained at 37° C. Using an isometric transducer ("TB-612J", manufactured by Nihon Kohden Corporation) and a pressure preamplifier ("AP-620G", manufactured by Nihon Kohden Corporation), variations in tension were measured. The isometric tensions were recorded on a thermal pen-writing recorder ("WT-647G", manufactured by Nihon Kohden Corporation). Taking the tonic contraction induced by $10^{-5}$ M norepinephrine (NE) as 100%, the percent contractions upon addition of each test drug at $10^{-8}$ M and $10^{-7}$ M were determined and recorded as α₁ action.

TABLE 7

| Comp'd No. | Anti 5-HT action (% of Control) | | Anti α₁ action (% of Control) | |
|---|---|---|---|---|
| | $10^{-7}$M | $10^{-6}$M | $10^{-8}$M | $10^{-7}$M |
| 22 | 75.3 | 21.3 | 91.2 | 64.9 |
| 25 | 69.8 | 19.6 | 65.3 | 24.1 |
| 26 | 54.6 | 18.2 | 99.6 | 73.1 |
| 27 | 76.2 | 22.7 | 91.2 | 53.0 |
| 30 | 83.5 | 37.2 | 102.3 | 88.0 |

Capability of Exploitation in Industry

The pyrrolesulfonamide derivatives (I) and their salts according to the present invention have strong serotonin-2 blocking action and have high safety. Accordingly, the present invention has made it possible to provide pharmaceuticals making use of antagonistic action against serotonin-2 receptors, for example, therapeutics for various circulatory diseases such as ischemic heart diseases, cerebrovascular disturbances and peripheral circulatory disturbances. Further, the compounds according to the present invention include those also having α₁ blocking action in combination. Since these compounds are also effective as antihypertensives, they are extremely used for therapeutics for a wide variety of circulatory diseases.

The invention claimed is:

1. A process for preparing a compound of formula (Ia):

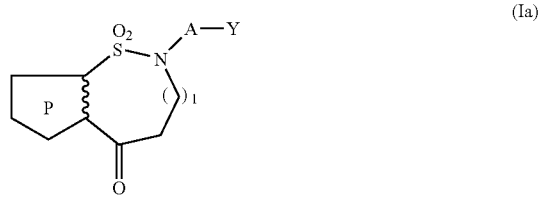

(Ia)

wherein
the ring P is:

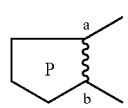

and is a pyrrole ring represented by the following structure:

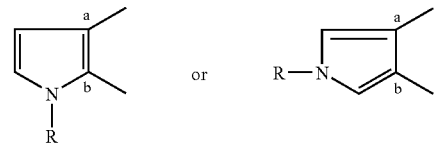

in which R is an alkyl group, a cycloalkyl group, a cycloalkyl-alkyl group or a substituted or unsubstituted aralkyl group;

A is a substituted or unsubstituted alkylene group, a substituted or unsubstituted alkenylene group or a substituted or unsubstituted alkynylene group;

Y is a group having the following formula:

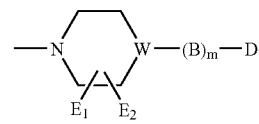

in which

E₁ and E₂ each independently is a hydrogen atom or a lower alkyl group;

W represents CH, C= or a nitrogen atom; with the provisos that:

when W represents CH, then m is 0 or 1 and B represents a carbonyl group, a sulfonyl group, an alkylene group, an alkenylene group, a group —C(OH)R₂— in which R₂ represents a substituted or unsubstituted aryl group, a group —CHR₃— in which R₃ represents a substituted or unsubstituted aryl group, or a substituted or unsubstituted cyclic or acyclic acetal group;

when W represents C=, then m is 1 and B is a group:

in which the double bond is coupled with W and R₄ represents a substituted or unsubstituted aryl group or a substituted or unsubstituted aralkyl group; and when W represents a nitrogen atom, then m is 0 or 1 and B is a carbonyl group, a sulfonyl group, an alkylene group, an alkenylene group or a group —CHR₅— in which R₅ represents a substituted or unsubstituted aryl group; and D represents a substituted or unsubstituted aromatic hydrocarbon group or a substituted or unsubstituted aromatic heterocyclic group; and l is 0 or 1;

which process comprises:

reacting a compound of formula (VI) with a compound of formula (II), wherein:

the compound of formula (VI) is:

X—A—Y  (VI), where

X is an eliminative group;

A and Y are defined above; and wherein the compound of formula (II) is:

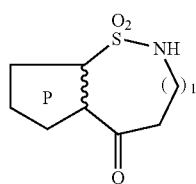
(II)

wherein the ring P and l are defined above.

2. A process for preparing a compound of formula (Ic):

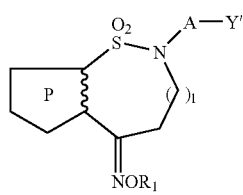
(Ic)

wherein
the ring P is:

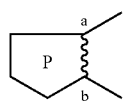

and is a pyrrole ring represented by the following structure:

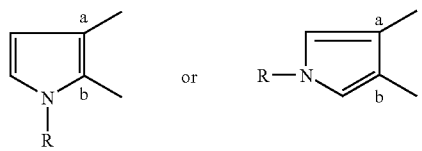

in which R is an alkyl group, a cycloalkyl group, a cycloalkyl-alkyl group or a substituted or unsubstituted aralkyl group;

$R_1$ is a hydrogen atom, a substituted or unsubstituted alkyl group, a substituted or unsubstituted aralkyl group, or a substituted or unsubstituted aryl group;

A is a substituted or unsubstituted alkylene group, a substituted or unsubstituted alkenylene group or a substituted or unsubstituted alkynylene group;

Y' represents a group

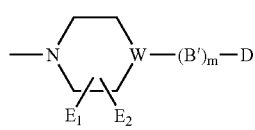

in which
$E_1$ and $E_2$ each independently is a hydrogen atom or a lower alkyl group;

W represents CH, C= or a nitrogen atom; with the provisos that:

when W represents CH, then m is 0 or 1 and B' represents a sulfonyl group, an alkylene group, an alkenylene group, a group —C(OH)$R_2$— in which $R_2$ represents a substituted or unsubstituted aryl group, a group —CHR$_3$— in which $R_3$ represents a substituted or unsubstituted aryl group, or a substituted or unsubstituted cyclic or acyclic acetal group;

when W represents C=, then m is 1 and B' is a group:

in which the double bond is coupled with W and $R_4$ represents a substituted or unsubstituted aryl group or a substituted or unsubstituted aralkyl group; and when W represents a nitrogen atom, then m is 0 or 1 and B' is a carbonyl group, a sulfonyl group, an alkylene group, an alkenylene group or a group —CHR$_5$— in which $R_5$ represents a substituted or unsubstituted aryl group; and D represents a substituted or unsubstituted aromatic hydrocarbon group or a substituted or unsubstituted aromatic heterocyclic group; and l is 0 or 1;

which process comprises:

reacting a compound of formula (VII) with a compound of formula (Ib), wherein the compound of formula (VII) is:

NH$_2$OR$_1$ (VII)

wherein $R_1$ is defined above; and the compound of formula (Ib) is:

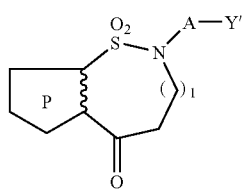
(Ib)

wherein the ring P, A, Y' and l are defined above.

3. A process for preparing a compound of formula (Id):

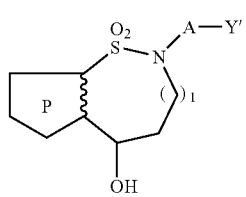
(Id)

wherein
the ring P is:

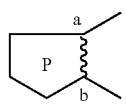

and is a pyrrole ring represented by the following structure:

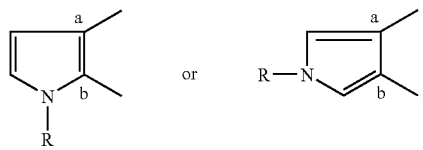

in which R is an alkyl group, a cycloalkyl group, a cycloalkyl-alkyl group or a substituted or unsubstituted aralkyl group;

A is a substituted or unsubstituted alkylene group, a substituted or unsubstituted alkenylene group or a substituted or unsubstituted alkynylene group;

Y' represents a group

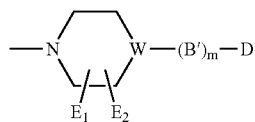

in which $E_1$ and $E_2$ each independently is a hydrogen atom or a lower alkyl group;

W represents CH, C= or a nitrogen atom; with the provisos that:

when W represents CH, then m is 0 or 1 and B' represents a sulfonyl group, an alkylene group, an alkenylene group, a group —C(OH)$R_2$— in which $R_2$ represents a substituted or unsubstituted aryl group, a group —CHR$_3$— in which $R_3$ represents a substituted or unsubstituted aryl group, or a substituted or unsubstituted cyclic or acyclic acetal group;

when W represents C=, then m is 1 and B' is a group:

in which the double bond is coupled with W and $R_4$ represents a substituted or unsubstituted aryl group or a substituted or unsubstituted aralkyl group; and when W represents a nitrogen atom, then m is 0 or 1 and B' is a carbonyl group, a sulfonyl group, an alkylene group, an alkenylene group or a group —CHR$_5$— in which $R_5$ represents a substituted or unsubstituted aryl group; and D represents a substituted or unsubstituted aromatic hydrocarbon group or a substituted or unsubstituted aromatic heterocyclic group; and l is 0 or 1;

which process comprises:
reducing a compound of formula (Ib):

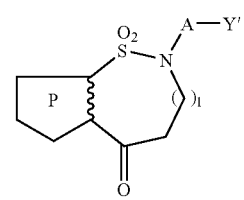

(Ib)

wherein the ring P, A, Y' and l are defined above.

4. A process for preparing a compound of formula (Ie):

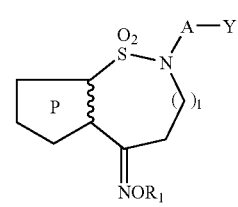

(Ie)

wherein
the ring P is:

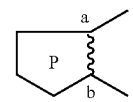

and is a pyrrole ring represented by the following structure:

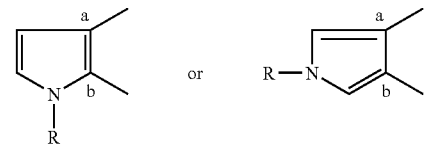

in which R is an alkyl group, a cycloalkyl group, a cycloalkyl-alkyl group or a substituted or unsubstituted aralkyl group;

$R_1$ is a hydrogen atom, a substituted or unsubstituted alkyl group, a substituted or unsubstituted aralkyl group, or a substituted or unsubstituted aryl group;

A is a substituted or unsubstituted alkylene group, a substituted or unsubstituted alkenylene group or a substituted or unsubstituted alkynylene group;

Y is a group having the following formula:

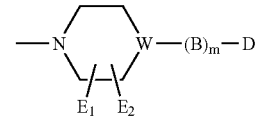

in which
$E_1$ and $E_2$ each independently is a hydrogen atom or a lower alkyl group;

W represents CH, C= or a nitrogen atom; with the provisos that:

when W represents CH, then m is 0 or 1 and B represents a carbonyl group, a sulfonyl group, an alkylene group, an alkenylene group, a group —C(OH)$R_2$— in which $R_2$ represents a substituted or unsubstituted aryl group, a group —$CHR_3$— in which $R_3$ represents a substituted or unsubstituted aryl group, or a substituted or unsubstituted cyclic or acyclic acetal group;

when W represents C=, then m is 1 and B is a group:

in which the double bond is coupled with W and $R_4$ represents a substituted or unsubstituted aryl group or a substituted or unsubstituted aralkyl group; and when W represents a nitrogen atom, then m is 0 or 1 and B is a carbonyl group, a sulfonyl group, an alkylene group, an alkenylene group or a group —$CHR_5$— in which $R_5$ represents a substituted or unsubstituted aryl group; and D represents a substituted or unsubstituted aromatic hydrocarbon group or a substituted or unsubstituted aromatic heterocyclic group; and l is 0 or 1;

which process comprises:

reacting a compound of formula (VII):

 (VII)

wherein $R_1$ is defined above, with a compound of formula (IV):

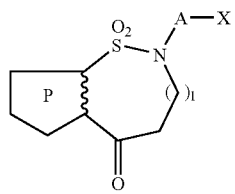 (IV)

wherein X is an eliminative group, and the ring P, A and l are defined above, thereby obtaining a compound represented by the following formula (VIII):

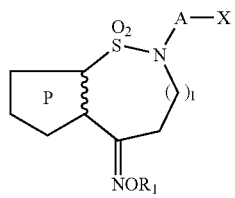 (VIII)

wherein the ring P, $R_1$, A, X and l are defined above; and then reacting the compound of formula (VIII) with a nitrogen-containing compound of formula (V):

 (V)

wherein Y is defined above.

5. A process for preparing a compound of formula (If):

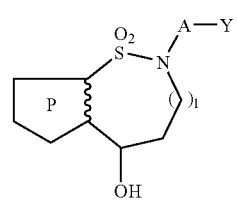 (If)

wherein the ring P is:

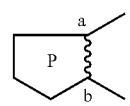

and is a pyrrole ring represented by the following structure:

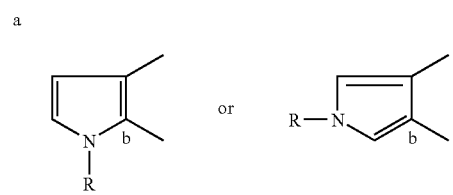

in which R is an alkyl group, a cycloalkyl group, a cycloalkyl-alkyl group or a substituted or unsubstituted aralkyl group;

A is a substituted or unsubstituted alkylene group, a substituted or unsubstituted alkenylene group or a substituted or unsubstituted alkynylene group;

Y is a group having the following formula:

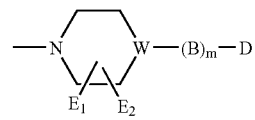

in which $E_1$ and $E_2$ each independently is a hydrogen atom or a lower alkyl group;

W represents CH, C= or a nitrogen atom; with the provisos that:

when W represents CH, then m is 0 or 1 and B represents a carbonyl group, a sulfonyl group, an alkylene group, an alkenylene group, a group —C(OH)$R_2$— in which $R_2$ represents a substituted or unsubstituted aryl group, a group —$CHR_3$— in which $R_3$ represents a substituted or unsubstituted aryl group, or a substituted or unsubstituted cyclic or acyclic acetal group;

when W represents C=, then m is 1 and B is a group:

in which the double bond is coupled with W and $R_4$ represents a substituted or unsubstituted aryl group or a substituted or unsubstituted aralkyl group; and when W represents a nitrogen atom, then m is 0 or 1 and B is a carbonyl group, a sulfonyl group, an alkylene group, an alkenylene group or a group —$CHR_5$— in which $R_5$ represents a substituted or unsubstituted aryl group; and D represents a substituted or unsubstituted aromatic hydrocarbon group or a substituted or unsubstituted aromatic heterocyclic group; and l is 0 or 1;

which process comprises:

reducing a compound of formula (IV):

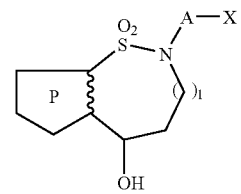
(IV)

wherein X is an eliminative group, and the ring P, A and l are defined above, thereby obtaining a compound of formula (IX):

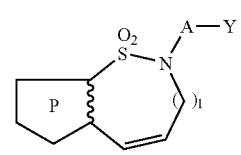
(IX)

wherein the ring P, A, X and l are defined above; and then reacting the compound of formula (IX) with a nitrogen-containing compound represented by the following formula (V):

H—Y (V)

wherein Y is defined above.

6. A process for preparing a compound of formula (Ig):

(Ig)

wherein
the ring P is:

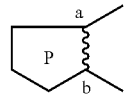

and is a pyrrole ring represented by the following structure:

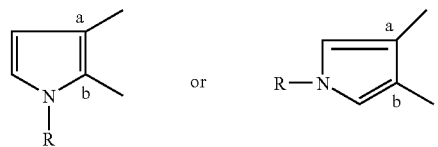

in which R is an alkyl group, a cycloalkyl group, a cycloalkyl-alkyl group or a substituted or unsubstituted aralkyl group;

A is a substituted or unsubstituted alkylene group, a substituted or unsubstituted alkenylene group or a substituted or unsubstituted alkynylene group;

Y is a group having the following formula:

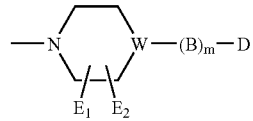

in which
$E_1$ and $E_2$ each independently is a hydrogen atom or a lower alkyl group;

W represents CH, C= or a nitrogen atom; with the provisos that:

when W represents CH, then m is 0 or 1 and B represents a carbonyl group, a sulfonyl group, an alkylene group, an alkenylene group, a group —C(OH)$R_2$— in which $R_2$ represents a substituted or unsubstituted aryl group, a group —$CHR_3$— in which $R_3$ represents a substituted or unsubstituted aryl group, or a substituted or unsubstituted cyclic or acyclic acetal group;

when W represents C=, then m is 1 and B is a group:

in which the double bond is coupled with W and $R_4$ represents a substituted or unsubstituted aryl group or a substituted or unsubstituted aralkyl group; and when W represents a nitrogen atom, then m is 0 or 1 and B is a carbonyl group, a sulfonyl group, an alkylene group, an alkenylene group or a group —$CHR_5$— in which $R_5$ represents a substituted or unsubstituted aryl group; and D represents a substituted or unsubstituted aromatic hydrocarbon group or a substituted or unsubstituted aromatic heterocyclic group; and l is 0 or 1;

which process comprises:

subjecting to a dehydration treatment a compound of formula (IX):

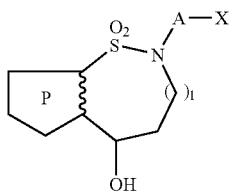
(IX)

wherein the ring P, A, and l are defined above, and X is an eliminative group, thereby obtaining a compound of formula (X):

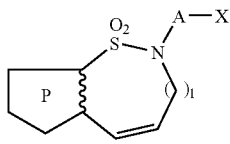
(X)

wherein the ring P, A, X and l have the same meanings as defined above; and then reacting the compound of formula (X) with a nitrogen-containing compound of formula (V):

H—Y    (V)

wherein Y is defined above.

7. A process for the preparation of a pyrrolesulfonamide derivative represented by the following formula (Ig):

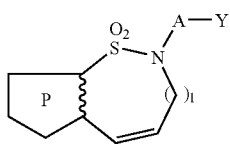
(Ig)

wherein
the ring P is:

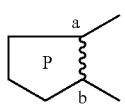

and is a pyrrole ring represented by the following structure:

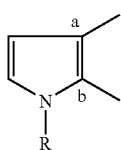 or 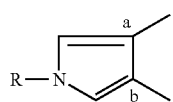

in which R is an alkyl group, a cycloalkyl group, a cycloalkyl-alkyl group or a substituted or unsubstituted aralkyl group;

A is a substituted or unsubstituted alkylene group, a substituted or unsubstituted alkenylene group or a substituted or unsubstituted alkynylene group;

Y is a group having the following formula:

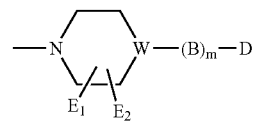

in which $E_1$ and $E_2$ each independently is a hydrogen atom or a lower alkyl group;

W represents CH, C= or a nitrogen atom; with the provisos that:

when W represents CH, then m is 0 or 1 and B represents a carbonyl group, a sulfonyl group, an alkylene group, an alkenylene group, a group —C(OH)$R_2$— in which $R_2$ represents a substituted or unsubstituted aryl group, a group —CHR$_3$— in which $R_3$ represents a substituted or unsubstituted aryl group, or a substituted or unsubstituted cyclic or acyclic acetal group;

when W represents C=, then m is 1 and B is a group:

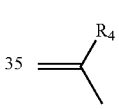

in which the double bond is coupled with W and $R_4$ represents a substituted or unsubstituted aryl group or a substituted or unsubstituted aralkyl group; and when W represents a nitrogen atom, then m is 0 or 1 and B is a carbonyl group, a sulfonyl group, an alkylene group, an alkenylene group or a group —CHR$_5$— in which $R_5$ represents a substituted or unsubstituted aryl group; and D represents a substituted or unsubstituted aromatic hydrocarbon group or a substituted or unsubstituted aromatic heterocyclic group; and l is 0 or 1;

which process comprises:

subjecting a compound of formula (If):

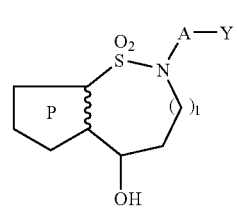
(If)

wherein the ring P, A, Y and l are defined above, to a dehydration treatment.

8. A compound represented by the following formula (II):

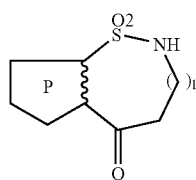

wherein
the ring P is:

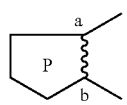

and is a pyrrole ring represented by the following structure:

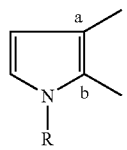 or 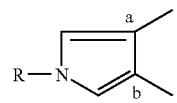

in which R is an alkyl group, a cycloalkyl group, a cycloalkyl-alkyl group or a substituted or unsubstituted aralkyl group; and l is 0 or 1.

9. A compound of formula (XI):

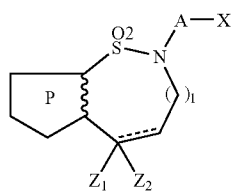

the ring P is:

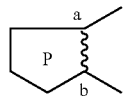

and is a pyrrole ring represented by the following structure:

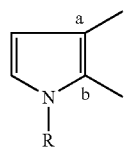 or 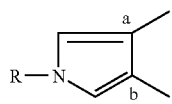

in which R is an alkyl group, a cycloalkyl group, a cycloalkyl-alkyl group or a substituted or unsubstituted aralkyl group;

$Z_1$ is a hydrogen atom and $Z_2$ is not present when the bond represented by the dashed line is present, and $Z_1$ is hydrogen and $Z_2$ is hydroxyl when the bond represented by the dashed line is not present or $Z_1$ and $Z_2$ together to represent an oxygen atom or a group $NOR_1$, where $R_1$ is a hydrogen atom, a substituted or unsubstituted alkyl group, a substituted or unsubstituted aralkyl group, or a substituted or unsubstituted aryl group;

A is a substituted or unsubstituted alkylene group, a substituted or unsubstituted alkenylene group or a substituted or unsubstituted alkynylene group;

X is an eliminative group; and l is 0 or 1.

10. A process for preparing a compound of formula (IIa) or (IIa'):

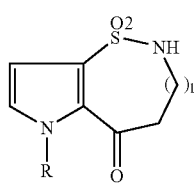

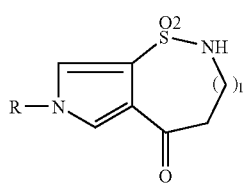

wherein R represents an alkyl group, a cycloalkyl group, a cycloalkyl-alkyl group or a substituted or unsubstituted aralkyl group and l is 0 or 1;

which process comprises:

converting a 1-substituted-pyrrole-3-sulfonic acid or a salt thereof of formula (XII):

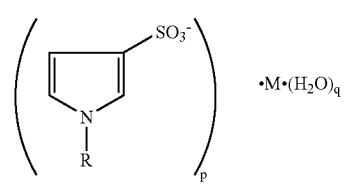

wherein M represents a hydrogen ion, an alkali metal ion, an alkaline earth metal ion or a quaternary ammonium ion, p is 1 when M is a hydrogen ion, an alkali metal ion or a quaternary ammonium ion or p is 2 when M is an alkaline earth metal ion, q is 0 or 1, and R has the same meaning as defined above, into a compound represented by formula (XIII):

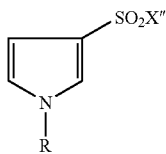
(XIII)

wherein X″ is a chlorine atom or a bromine atom;
thus causing glycine or β-alknine or a derivative thereof of formula (XIV):

$NH_2(CH_2)_lCH_2COOR_6$ (XIV)

wherein $R_6$ represents a hydrogen atom or a carboxyl-protecting group,
to act, thereby obtaining a compound of formula (XV):

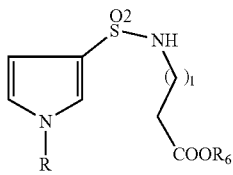
(XV)

wherein R, $R_6$ and l are defined above; and then subjecting said compound to ring closure.

11. A process for preparing a compound of formula (IIa) or (IIa'):

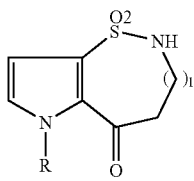
(IIa)

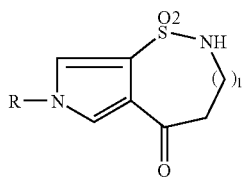
(IIa')

wherein
R represents an alkyl group, a cycloalkyl group, a cycloalkyl-alkyl group or a substituted or unsubstituted aralkyl group and
l is 0 or 1;
which process comprises:
reacting a compound of formula (XVIa) or (XVIb):

R—X‴ (XVIa)

$(RO)_2SO_2$ (XVIb)

wherein X‴ is an eliminative group and R is defined above,
with a compound of formula (IIb) or (IIb'):

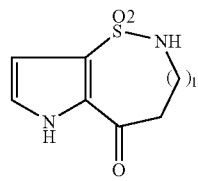
(IIb)

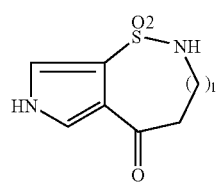
(IIb')

wherein l is defined above.

12. A compound of formula (XV):

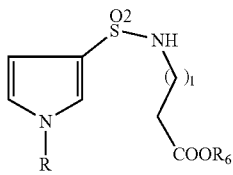
(XV)

R represents an alkyl group, a cycloalkyl group, a cycloalkyl-alkyl group or a substituted or unsubstituted aralkyl group;
$R_6$ represents a hydrogen atom or a carboxyl-protecting group; and
l is 0 or 1.

* * * * *

UNITED STATES PATENT AND TRADEMARK OFFICE
CERTIFICATE OF CORRECTION

PATENT NO. : 7,057,036 B2
APPLICATION NO. : 10/615836
DATED : June 6, 2006
INVENTOR(S) : Akira Mizuno et al.

It is certified that error appears in the above-identified patent and that said Letters Patent is hereby corrected as shown below:

On the title page, Item (73), the Assignee is incorrect. Item (73) should read:

-- (73) Assignee: Daiichi Asubio Pharma Co., Ltd., Tokyo (JP)--; and

Item (65), Prior Publication Data should read:

--US 2005/0038242 A2 February 17, 2005
US 2004/0127705 A1 July 1, 2004--

Signed and Sealed this

Sixth Day of February, 2007

JON W. DUDAS
*Director of the United States Patent and Trademark Office*